(12) United States Patent
Porchia et al.

(10) Patent No.: US 8,320,751 B2
(45) Date of Patent: Nov. 27, 2012

(54) VOLATILE MATERIAL DIFFUSER AND METHOD OF PREVENTING UNDESIRABLE MIXING OF VOLATILE MATERIALS

(75) Inventors: Jose Porchia, Greenfield, WI (US); Pedro Emanuel Vasconcelos de Queiroz Vieira, Cascais (PT); Martin S. Payne, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1071 days.

(21) Appl. No.: 12/288,606

(22) Filed: Oct. 22, 2008

(65) Prior Publication Data

US 2009/0162253 A1 Jun. 25, 2009

Related U.S. Application Data

(60) Provisional application No. 61/008,613, filed on Dec. 20, 2007, provisional application No. 61/067,571, filed on Feb. 28, 2008.

(51) Int. Cl.
*F24F 6/08* (2006.01)
(52) U.S. Cl. .......................................... 392/395; 392/386
(58) Field of Classification Search ........................ None
See application file for complete search history.

(56) References Cited

U.S. PATENT DOCUMENTS

| | | |
|---|---|---|
| 1,112,807 A | 10/1914 | King |
| 1,204,934 A | 11/1916 | Burford et al. |
| 1,763,374 A | 6/1930 | Schrader |
| 1,829,714 A | 10/1931 | McElroy et al. |
| 1,947,752 A | 2/1934 | Benesh |
| 2,084,682 A | 6/1937 | Guenot |
| 2,094,161 A | 9/1937 | Paddock |
| 2,103,609 A | 12/1937 | Bradburn |
| 2,221,876 A | 11/1940 | Mackin |
| 2,301,691 A | 11/1942 | Ellinger et al. |
| 2,555,047 A | 5/1951 | Logue |
| 2,600,877 A | 6/1952 | Jeffree |
| 2,608,436 A | 8/1952 | Baughman |
| 2,686,944 A | 8/1954 | Gubelin |
| 2,715,056 A | 8/1955 | Wilson |
| 2,741,004 A | 4/1956 | Williams |
| 2,905,049 A | 9/1959 | Laube |
| 3,118,610 A | 1/1964 | Techler |

(Continued)

FOREIGN PATENT DOCUMENTS

EP 911 041 4/1999

(Continued)

OTHER PUBLICATIONS

PCT/US2008/013813 International Search Report and Written Opinion dated Mar. 18, 2009.

*Primary Examiner* — Thor Campbell

(57) ABSTRACT

A volatile material diffuser includes a housing and first and second containers holding first and second volatile materials and having first and second wicks, respectively, in contact with respective volatile materials and extending out of respective containers, wherein the containers are inserted into and detachably attached to the housing. The diffuser further includes first and second heaters disposed within the housing adjacent the first and second wicks, respectively, to vaporize the first and second volatile materials, respectively. A means for providing an air flow is disposed in the housing such that air from the means for providing an air flow transports vaporized volatile materials away from the housing. The heaters are energized in an alternating sequence such that, when a heater is deactivated, the means for providing an air flow cools a wick associated with the deactivated heater.

20 Claims, 22 Drawing Sheets

U.S. PATENT DOCUMENTS

| | | |
|---|---|---|
| 3,172,604 A | 3/1965 | Brock |
| 3,301,486 A | 1/1967 | Brock |
| 3,370,571 A | 2/1968 | Knapp |
| 3,375,774 A | 4/1968 | Fujimura et al. |
| 3,383,178 A | 5/1968 | Dietz |
| 3,410,488 A | 11/1968 | Sugimura |
| 3,414,864 A | 12/1968 | Barrington |
| 3,447,505 A | 6/1969 | Wagner |
| 3,612,356 A | 10/1971 | McVey |
| 3,628,829 A | 12/1971 | Hellig |
| 3,655,135 A | 4/1972 | Altman et al. |
| 3,711,023 A | 1/1973 | Smith |
| 3,763,888 A | 10/1973 | Duecker |
| 3,812,996 A | 5/1974 | Bunnell |
| 3,844,057 A | 10/1974 | Johnson |
| 3,917,396 A | 11/1975 | Donohue et al. |
| 3,972,473 A | 8/1976 | Harrison |
| 4,065,656 A | 12/1977 | Brown et al. |
| 4,078,891 A | 3/1978 | Madjar |
| 4,084,732 A | 4/1978 | Dearling |
| 4,123,741 A | 10/1978 | Kiyono et al. |
| 4,229,415 A | 10/1980 | Bryson |
| 4,235,373 A | 11/1980 | Clark |
| 4,391,390 A | 7/1983 | Howard |
| 4,456,176 A | 6/1984 | Agius |
| 4,545,396 A | 10/1985 | Miller et al. |
| 4,556,539 A | 12/1985 | Spector |
| 4,580,721 A | 4/1986 | Coffee et al. |
| 4,588,874 A | 5/1986 | Napierski |
| 4,603,030 A | 7/1986 | McCarthy |
| 4,614,300 A | 9/1986 | Falcoff |
| 4,629,164 A | 12/1986 | Sommerville |
| 4,629,604 A | 12/1986 | Spector |
| 4,680,060 A | 7/1987 | Gupta et al. |
| 4,695,434 A | 9/1987 | Spector |
| 4,730,103 A | 3/1988 | Hawkins |
| 4,731,520 A | 3/1988 | Glucksman et al. |
| 4,755,404 A | 7/1988 | Collette |
| 4,795,883 A | 1/1989 | Glucksman et al. |
| 4,798,935 A | 1/1989 | Pezaris |
| 4,804,821 A | 2/1989 | Glucksman |
| 4,846,403 A | 7/1989 | Mivelaz |
| 4,852,802 A | 8/1989 | Iggulden et al. |
| 4,870,991 A | 10/1989 | McMillan et al. |
| D304,758 S | 11/1989 | Glucksman et al. |
| 4,881,568 A | 11/1989 | Ho |
| 4,893,615 A | 1/1990 | Khabirova |
| 4,901,890 A | 2/1990 | Mivelaz |
| 4,905,112 A | 2/1990 | Rhodes |
| 4,913,034 A | 4/1990 | Ripple et al. |
| 5,011,632 A | 4/1991 | Yano et al. |
| 5,022,585 A | 6/1991 | Burgess |
| 5,023,020 A | 6/1991 | Machida et al. |
| 5,038,394 A | 8/1991 | Hasegawa et al. |
| 5,038,972 A | 8/1991 | Muderlak et al. |
| 5,050,798 A | 9/1991 | Sullivan |
| 5,071,621 A | 12/1991 | Tokuhiro et al. |
| 5,097,375 A | 3/1992 | Khan |
| 5,105,133 A | 4/1992 | Yang |
| 5,111,477 A | 5/1992 | Muderlak |
| 5,115,975 A | 5/1992 | Shilling |
| 5,133,498 A | 7/1992 | Sealy et al. |
| 5,152,397 A | 10/1992 | Mayled |
| D330,758 S | 11/1992 | Muderlak |
| 5,163,616 A | 11/1992 | Bernarducci et al. |
| 5,167,877 A | 12/1992 | Pai |
| 5,175,791 A | 12/1992 | Muderlak et al. |
| 5,178,327 A | 1/1993 | Palamand et al. |
| 5,186,869 A | 2/1993 | Stumpf et al. |
| 5,192,342 A | 3/1993 | Baron et al. |
| 5,193,744 A | 3/1993 | Goldstein |
| 5,201,025 A | 4/1993 | Landesberg |
| 5,212,672 A | 5/1993 | Loisch et al. |
| 5,222,186 A | 6/1993 | Schimanski et al. |
| 5,227,068 A | 7/1993 | Runyon |
| 5,230,837 A | 7/1993 | Babasade |
| 5,234,162 A | 8/1993 | Sullivan |
| 5,314,619 A | 5/1994 | Runyon |
| 5,314,669 A | 5/1994 | Hamilton |
| 5,321,669 A | 6/1994 | Thayer et al. |
| 5,342,584 A | 8/1994 | Fritz et al. |
| 5,343,747 A | 9/1994 | Rosen |
| 5,364,027 A | 11/1994 | Kuhn |
| 5,377,363 A | 1/1995 | Shieh |
| 5,398,070 A | 3/1995 | Lee |
| D359,346 S | 6/1995 | Martin |
| 5,434,386 A | 7/1995 | Glenn et al. |
| 5,438,914 A | 8/1995 | Hohn et al. |
| 5,449,117 A | 9/1995 | Muderlak et al. |
| D364,450 S | 11/1995 | Kearnes |
| 5,518,790 A | 5/1996 | Huber et al. |
| 5,521,357 A | 5/1996 | Lock et al. |
| 5,524,609 A | 6/1996 | Krull |
| 5,565,148 A | 10/1996 | Pendergrass, Jr. |
| 5,574,821 A | 11/1996 | Babasade |
| 5,591,409 A | 1/1997 | Watkins |
| 5,603,513 A | 2/1997 | Shekleton et al. |
| 5,660,330 A | 8/1997 | Scott |
| 5,666,987 A | 9/1997 | Combs |
| D385,024 S | 10/1997 | Roberts |
| 5,680,409 A | 10/1997 | Qin et al. |
| 5,695,692 A | 12/1997 | Kennedy |
| D393,063 S | 3/1998 | Wefler |
| 5,724,256 A | 3/1998 | Lee et al. |
| 5,725,472 A | 3/1998 | Weathers |
| 5,727,186 A | 3/1998 | Shervington et al. |
| 5,734,590 A | 3/1998 | Tebbe |
| 5,762,268 A | 6/1998 | Shervington et al. |
| 5,772,074 A | 6/1998 | Dial et al. |
| 5,805,768 A | 9/1998 | Schwartz et al. |
| 5,810,201 A | 9/1998 | Besse et al. |
| 5,816,446 A | 10/1998 | Steindorf et al. |
| 5,832,320 A | 11/1998 | Wittek |
| 5,887,118 A | 3/1999 | Huffman et al. |
| 5,894,841 A | 4/1999 | Voges |
| 5,899,381 A | 5/1999 | Gordon et al. |
| 5,899,382 A | 5/1999 | Hayes et al. |
| 5,948,989 A | 9/1999 | Ichikawa et al. |
| 5,949,522 A | 9/1999 | Manne |
| 5,956,663 A | 9/1999 | Eryurek |
| 5,972,290 A | 10/1999 | De Sousa |
| 5,975,675 A | 11/1999 | Kim |
| 6,000,658 A | 12/1999 | McCall, Jr. |
| 6,012,005 A | 1/2000 | Gscheidle et al. |
| 6,017,143 A | 1/2000 | Eryurek et al. |
| 6,039,212 A | 3/2000 | Singh |
| 6,041,659 A | 3/2000 | Wilda et al. |
| 6,053,738 A | 4/2000 | Ivey, Jr. |
| 6,104,867 A | 8/2000 | Stathakis et al. |
| 6,106,786 A | 8/2000 | Akahoshi |
| 6,119,047 A | 9/2000 | Eryurek et al. |
| 6,123,935 A | 9/2000 | Wefler et al. |
| 6,136,277 A | 10/2000 | Nardini |
| 6,141,496 A | 10/2000 | Sundberg et al. |
| D434,485 S | 11/2000 | Furner |
| 6,172,343 B1 | 1/2001 | Nothe et al. |
| D437,636 S | 2/2001 | Basaganas |
| 6,189,810 B1 | 2/2001 | Nerushai et al. |
| 6,196,218 B1 | 3/2001 | Voges |
| 6,231,032 B1 | 5/2001 | Ivey, Jr. |
| 6,234,455 B1 | 5/2001 | Wittek |
| 6,236,807 B1 | 5/2001 | Ruffolo et al. |
| 6,241,944 B1 | 6/2001 | Budman |
| 6,254,065 B1 | 7/2001 | Ehrensperger et al. |
| 6,278,840 B1 | 8/2001 | Basaganas Millan |
| 6,279,836 B1 | 8/2001 | Toetschinger et al. |
| 6,289,176 B1 | 9/2001 | Martter et al. |
| D449,101 S | 10/2001 | Wolpert et al. |
| 6,296,196 B1 | 10/2001 | Denen et al. |
| D451,990 S | 12/2001 | Millet |
| 6,328,287 B2 | 12/2001 | Wittek |
| 6,338,818 B2 | 1/2002 | Budman |
| 6,349,168 B1 | 2/2002 | Jaworski |
| 6,357,726 B1 | 3/2002 | Watkins |
| 6,361,752 B1 | 3/2002 | Demarest et al. |
| 6,368,564 B1 | 4/2002 | Smith |
| 6,371,451 B1 | 4/2002 | Choi |

| | | |
|---|---|---|
| 6,379,242 B1 | 4/2002 | Wiseman, Sr. et al. |
| 6,390,453 B1 | 5/2002 | Frederickson |
| 6,406,004 B1 | 6/2002 | Ude |
| 6,409,093 B2 | 6/2002 | Ulczynski et al. |
| D461,549 S | 8/2002 | Garcia |
| D463,437 S | 9/2002 | Bush et al. |
| 6,446,583 B2 | 9/2002 | Vieira |
| D464,130 S | 10/2002 | Denham et al. |
| D466,204 S | 11/2002 | Wolpert et al. |
| 6,487,367 B2 | 11/2002 | Vieira |
| 6,501,052 B2 | 12/2002 | Cox et al. |
| 6,501,906 B2 | 12/2002 | Vieira |
| 6,502,762 B2 | 1/2003 | Tuttobene, Jr. |
| 6,511,531 B1 | 1/2003 | Cartellone |
| 6,533,193 B2 | 3/2003 | White |
| 6,536,746 B2 | 3/2003 | Watkins |
| D473,638 S | 4/2003 | Cruver |
| 6,542,442 B2 | 4/2003 | Kaslon |
| 6,555,068 B2 | 4/2003 | Smith |
| 6,556,272 B1 | 4/2003 | Du et al. |
| 6,563,091 B2 | 5/2003 | Vieira |
| 6,568,659 B2 | 5/2003 | Hugon |
| 6,569,387 B1 | 5/2003 | Furner et al. |
| RE38,150 E | 6/2003 | Greatbatch |
| 6,581,915 B2 | 6/2003 | Bartsch et al. |
| 6,592,104 B2 | 7/2003 | Cox |
| 6,602,475 B1 | 8/2003 | Chiao |
| 6,603,924 B2 | 8/2003 | Brown et al. |
| 6,610,254 B1 | 8/2003 | Furner et al. |
| 6,619,559 B2 | 9/2003 | Wohrle |
| 6,654,664 B1 | 11/2003 | Chiao |
| 6,661,967 B2 | 12/2003 | Levine et al. |
| 6,672,129 B1 | 1/2004 | Frederickson |
| 6,712,287 B1 | 3/2004 | Le Pesant et al. |
| 6,713,024 B1 | 3/2004 | Arnell et al. |
| 6,728,478 B2 | 4/2004 | Cox et al. |
| 6,741,919 B1 | 5/2004 | Schuster et al. |
| 6,773,679 B2 | 8/2004 | Jaworski et al. |
| 6,782,194 B2 | 8/2004 | Schneiderbauer |
| 6,783,081 B2 | 8/2004 | Pedrotti et al. |
| 6,783,117 B2 | 8/2004 | Wohrle |
| 6,786,474 B2 | 9/2004 | Watkins et al. |
| 6,790,011 B1 | 9/2004 | Le Pesant et al. |
| 6,790,408 B2 | 9/2004 | Whitby et al. |
| 6,792,199 B2 | 9/2004 | Levine et al. |
| 6,802,460 B2 | 10/2004 | Hess et al. |
| 6,803,987 B2 | 10/2004 | Manne |
| 6,805,300 B2 | 10/2004 | Munroe et al. |
| 6,832,794 B2 | 12/2004 | He et al. |
| 6,834,847 B2 | 12/2004 | Bartsch et al. |
| 6,842,218 B1 | 1/2005 | Manne |
| 6,843,430 B2 | 1/2005 | Boticki et al. |
| 6,843,537 B2 | 1/2005 | Babala et al. |
| 6,854,717 B2 | 2/2005 | Millan |
| 6,859,615 B2 | 2/2005 | Yip et al. |
| 6,862,403 B2 | 3/2005 | Pedrotti et al. |
| 6,871,794 B2 | 3/2005 | McEwen |
| 6,889,003 B2 | 5/2005 | Triplett et al. |
| 6,896,196 B2 | 5/2005 | Vieira |
| 6,912,355 B2 | 6/2005 | Vieira |
| 6,913,733 B2 | 7/2005 | Hardy et al. |
| 6,917,754 B2 | 7/2005 | Pedrotti et al. |
| 6,920,282 B2 | 7/2005 | He et al. |
| 6,931,202 B2 | 8/2005 | Pedrotti et al. |
| 6,950,607 B2 | 9/2005 | Yip et al. |
| 6,959,607 B2 | 11/2005 | Wilda |
| 7,011,795 B2 | 3/2006 | Thompson et al. |
| 7,014,818 B2 | 3/2006 | Rymer |
| 7,021,494 B2 | 4/2006 | Mazooji et al. |
| 7,032,831 B2 | 4/2006 | Duston et al. |
| D521,621 S | 5/2006 | Slater |
| 7,036,800 B2 | 5/2006 | Ellis |
| D529,159 S | 9/2006 | Howansky et al. |
| 7,132,084 B1 | 11/2006 | Roumpos |
| 7,133,605 B2 | 11/2006 | Niemeyer |
| 7,157,057 B2 | 1/2007 | Gohil |
| 7,160,515 B2 | 1/2007 | Murdell et al. |
| 7,175,815 B2 | 2/2007 | Yamasaki et al. |
| 7,190,888 B2 | 3/2007 | Wolf et al. |
| 7,201,333 B2 | 4/2007 | Yoshikawa et al. |
| D542,902 S | 5/2007 | Caserta et al. |
| D542,903 S | 5/2007 | Caserta et al. |
| 7,223,361 B2 | 5/2007 | Kvietok et al. |
| 7,249,719 B2 | 7/2007 | He et al. |
| D548,318 S | 8/2007 | Copeman |
| 7,277,626 B2 | 10/2007 | Pesu et al. |
| 7,309,024 B2 | 12/2007 | Hansen et al. |
| 7,341,698 B2 | 3/2008 | Pedrotti et al. |
| 7,344,123 B2 | 3/2008 | Pankhurst et al. |
| 7,357,561 B2 | 4/2008 | Hidalgo et al. |
| 7,376,344 B2 | 5/2008 | Manne |
| 7,387,265 B2 | 6/2008 | Hess et al. |
| 7,389,943 B2 | 6/2008 | Jaworski |
| RE40,464 E | 8/2008 | Vieira |
| 2001/0048037 A1 | 12/2001 | Bell et al. |
| 2002/0066798 A1 | 6/2002 | Laudamiel-Pellet et al. |
| 2002/0068009 A1 | 6/2002 | Laudamiel-Pellet et al. |
| 2002/0068010 A1 | 6/2002 | Laudamiel-Pellet et al. |
| 2002/0114744 A1 | 8/2002 | Chiao et al. |
| 2003/0091093 A1 | 5/2003 | Zitzmann et al. |
| 2003/0095895 A1 | 5/2003 | O'Loughlin |
| 2003/0107139 A1 | 6/2003 | Wohrle |
| 2003/0164557 A1 | 9/2003 | Chung et al. |
| 2003/0175148 A1 | 9/2003 | Kvietok |
| 2003/0206834 A1 | 11/2003 | Chiao et al. |
| 2004/0007787 A1 | 1/2004 | Kvietok et al. |
| 2004/0009103 A1 | 1/2004 | Westring |
| 2004/0028551 A1 | 2/2004 | Kvietok |
| 2004/0033171 A1 | 2/2004 | Kvietok |
| 2004/0055360 A1 | 3/2004 | Modien et al. |
| 2004/0101447 A1 | 5/2004 | Tajima et al. |
| 2004/0131509 A1 | 7/2004 | He et al. |
| 2004/0223871 A1 | 11/2004 | Woo et al. |
| 2004/0223891 A1 | 11/2004 | Brown |
| 2004/0247301 A1 | 12/2004 | Yip |
| 2004/0265164 A1 | 12/2004 | Woo et al. |
| 2005/0047956 A1 | 3/2005 | Samii |
| 2005/0147523 A1 | 7/2005 | Laudamiel-Pellet et al. |
| 2005/0147539 A1 | 7/2005 | Laudamiel-Pellet et al. |
| 2005/0161522 A1 | 7/2005 | Kvietok et al. |
| 2005/0167860 A1 | 8/2005 | Brooks |
| 2005/0201944 A1 | 9/2005 | Kvietok et al. |
| 2005/0211790 A1 | 9/2005 | Kvietok et al. |
| 2005/0214158 A1 | 9/2005 | Kvietok et al. |
| 2006/0018786 A1 | 1/2006 | Tolman et al. |
| 2006/0032937 A1 | 2/2006 | Caserta et al. |
| 2006/0067859 A1 | 3/2006 | Laudamiel-Pellet et al. |
| 2006/0074742 A1 | 4/2006 | Santandrea |
| 2006/0081721 A1 | 4/2006 | Caserta et al. |
| 2006/0091570 A1 | 5/2006 | Reece |
| 2006/0097065 A1 | 5/2006 | Kvietok et al. |
| 2006/0097066 A1 | 5/2006 | Kvietok et al. |
| 2006/0110144 A1 | 5/2006 | Fellows et al. |
| 2006/0153731 A1 | 7/2006 | Brown et al. |
| 2006/0153741 A1 | 7/2006 | Yoshida |
| 2006/0153744 A1 | 7/2006 | Thompson et al. |
| 2006/0193611 A1 | 8/2006 | Ruiz Ballesteros et al. |
| 2006/0210421 A1 | 9/2006 | Hammond et al. |
| 2006/0280659 A1 | 12/2006 | Brown et al. |
| 2007/0012718 A1 | 1/2007 | Schramm |
| 2007/0031298 A1 | 2/2007 | Roumpos et al. |
| 2007/0036688 A1 | 2/2007 | Hayes-Pankhurst |
| 2007/0047931 A1 | 3/2007 | Niemeyer |
| 2007/0048173 A1 | 3/2007 | Keller, Jr. et al. |
| 2007/0057084 A1 | 3/2007 | Vieira |
| 2007/0076440 A1 | 4/2007 | Chien |
| 2007/0079046 A1 | 4/2007 | Yang |
| 2007/0160492 A1 | 7/2007 | Spector |
| 2007/0176015 A1 | 8/2007 | Farrell et al. |
| 2007/0237499 A1 | 10/2007 | DeWitt et al. |
| 2007/0247555 A1 | 10/2007 | Diersing et al. |
| 2007/0257130 A1 | 11/2007 | Butler et al. |
| 2007/0280653 A1 | 12/2007 | Viera |
| 2008/0031784 A1 | 2/2008 | Bistritzky et al. |
| 2008/0049387 A1 | 2/2008 | Lee |
| 2008/0056691 A1 | 3/2008 | Wingo et al. |
| 2008/0069725 A1 | 3/2008 | Kvietok |

| | | | |
|---|---|---|---|
| 2008/0164337 A1 | 7/2008 | Brown et al. | |
| 2008/0190935 A1 | 8/2008 | Pankhurst et al. | |
| 2008/0191370 A1 | 8/2008 | Pankhurst et al. | |

FOREIGN PATENT DOCUMENTS

| | | |
|---|---|---|
| EP | 943 344 | 9/1999 |
| EP | 962 132 | 12/1999 |
| EP | 1 108 358 | 6/2001 |
| EP | 1 195 169 | 4/2002 |
| EP | 1 247 446 | 10/2002 |
| EP | 1 247 447 | 10/2002 |
| EP | 1 331 014 | 7/2003 |
| EP | 1 516 633 | 3/2005 |
| GB | 2 279 010 | 12/1994 |
| GB | 2 347 860 | 9/2000 |
| JP | 64-39745 | 3/1989 |
| JP | 3-147731 | 6/1991 |
| JP | 6-205929 | 7/1994 |
| JP | 11-000391 | 1/1999 |
| JP | 2001-231425 | 8/2001 |
| JP | 2005-503894 | 2/2005 |
| WO | WO 91/15249 | 10/1991 |
| WO | WO 97/38576 | 10/1997 |
| WO | WO 98/19526 | 5/1998 |
| WO | WO 98/46821 | 10/1998 |
| WO | WO 98/58692 | 12/1998 |
| WO | 0232472 A | 4/2002 |
| WO | WO 03/028775 | 4/2003 |
| WO | WO 2004/096300 | 11/2004 |
| WO | WO 2005/092400 | 10/2005 |
| WO | WO 2006/026637 | 3/2006 |
| WO | WO 2006/032709 | 3/2006 |
| WO | WO 2006/084921 | 8/2006 |
| WO | WO 2006/105347 | 10/2006 |
| WO | WO 2007/064188 | 6/2007 |
| WO | WO 2007/064189 | 6/2007 |
| WO | WO 2007/064197 | 6/2007 |
| WO | WO 2007/064199 | 6/2007 |
| WO | WO 2007/079046 | 7/2007 |
| WO | WO 2007/128146 | 11/2007 |
| WO | WO 2007/128147 | 11/2007 |
| WO | WO 2007/128148 | 11/2007 |
| WO | WO 2008/014812 | 2/2008 |

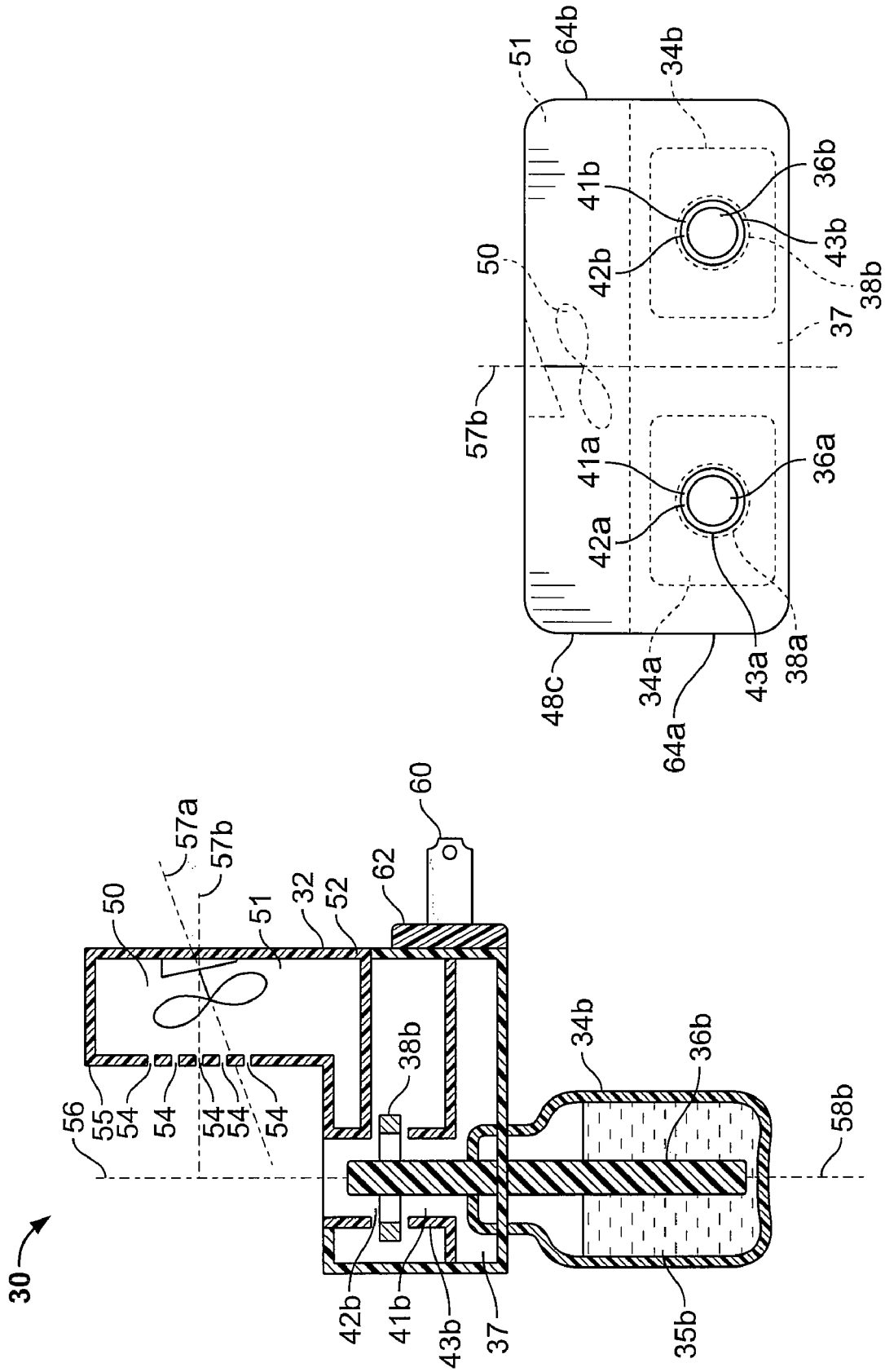

VOLATILE MATERIAL DIFFUSER AND METHOD OF PREVENTING UNDESIRABLE MIXING OF VOLATILE MATERIALS

CROSS REFERENCE TO RELATED APPLICATIONS

This application claims the benefit of U.S. Provisional Application No. 61/008 613 filed Dec. 20, 2007, and U.S. Provisional Application No. 61/067 571 filed Feb. 28, 2008. Each of the aforementioned applications is incorporated herein by reference in its entirety.

REFERENCE REGARDING FEDERALLY SPONSORED RESEARCH OR DEVELOPMENT

Not applicable

SEQUENTIAL LISTING

Not applicable

BACKGROUND

1. Field of the Invention

The present invention relates to volatile material diffusers, and more particularly, volatile material diffusers for dispensing volatile materials from more than one container.

2. Description of the Background

A multitude of volatile material diffusion devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing volatile materials from volatile material diffusers are also known in the art. For example, some diffusers include a heating element for heating a volatile material to promote vaporization thereof. Other diffusers employ a fan or blower to generate air flow to direct volatile material out of the diffuser into the surrounding environment. In another type of diffuser, one or more volatile materials may be emitted from the diffuser using a bolus generator that delivers a pulse of air to eject a scent ring. Still other diffusers that dispense volatile materials utilize ultrasonic means to dispense the volatile materials therefrom. In addition, other diffusers utilize more than one of these means to vaporize and/or disperse volatile materials.

In the past, such means have been utilized to dispense one or more volatile materials from a single diffuser. Multiple volatile materials have been used to prevent habituation, which is a phenomenon that occurs when a person becomes used to a particular volatile material such that they no longer perceive that volatile material.

One such device for emitting multiple volatile materials includes a multi-aroma cartridge having a frame with sections containing absorbent material saturated with different fragrances. The cartridge is inserted into a device having heaters disposed beneath each of the sections containing absorbent material. The heaters are actuated to dispense different fragrances.

One multi-fragrancing device includes two containers each having a wick extending therefrom and in contact with fragrances with the containers. Ring heaters are disposed around each of the wicks to vaporize fragrance disposed within the respective wicks. Energy is continuously supplied to a first of the heaters to continuously supply a first of the fragrances and energy is intermittently supplied to a second of the heaters to intermittently supply a second of the fragrances. The intermittent supply of the second fragrance prevents habituation with respect to the first fragrance by periodically supplying the second fragrance.

A further multi-fragrancing device includes first and second containers having first and second wicks respectively extending therefrom and in contact with first and second volatile materials disposed in the first and second containers, respectively. First and second heaters are disposed adjacent the first and second wicks, respectively, wherein the first and second heaters are alternately energized to alternately vaporize and disperse the first and second fragrances. In this device, the alternation of fragrances for a period of time, such as between 15 minutes and 2 hours, prevents habituation with respect to both of the fragrances.

Another multi-fragrancing device utilizes both heat and air flow to vaporize and disperse fragrances. Two containers having wicks extending therefrom and in contact with fragrances in the containers are disposed within the device. One or more heaters are disposed adjacent the wicks and one or more fans are disposed behind the wicks. A wall is disposed above the wicks to allow vaporized fragrance therethrough for dispersion by the one or more fans. The wall prevents air flow from the fan from cooling the heaters and/or wicks.

SUMMARY OF THE INVENTION

According to one aspect of the present invention, a volatile material diffuser includes a housing and first and second containers holding first and second volatile materials and having first and second wicks, respectively, in contact with respective volatile materials and extending out of respective containers, wherein the containers are inserted into and detachably attached to the housing. The diffuser further includes first and second heaters disposed within the housing adjacent the first and second wicks, respectively, to vaporize the first and second volatile materials, respectively. A means for providing an air flow is disposed in the housing such that air from the means for providing an air flow transports vaporized volatile materials away from the housing. The heaters are energized in an alternating sequence such that, when a heater is deactivated, the means for providing an air flow cools a wick associated with the deactivated heater.

According to another aspect of the present invention, a volatile material diffuser includes a housing and first and second containers holding first and second volatile materials and having first and second wicks, respectively, in contact with respective volatile materials and extending out of respective containers, wherein the containers are inserted into and detachably attached to the housing. First and second heaters are disposed within the housing adjacent the first and second wicks, respectively, to vaporize the first and second volatile materials, respectively. A fan is disposed in the housing such that air from the fan exhausts vaporized volatile materials from the housing. When the first heater is deactivated and the second heater is activated, the fan acts to cool the first wick to reduce temperatures of the first wick and the first heater to minimize the amount of the first volatile material that is emitted while the second volatile material is being emitted.

According to yet another aspect of the present invention, a method of preventing undesired mixing of volatile materials includes the step of providing a volatile material diffuser having a housing and two containers detachably attached to the housing and including volatile materials and wicks in contact with the volatile materials and extending out of the containers. The method further includes the steps of providing heaters disposed adjacent the wicks and providing a fan spaced above the wicks and heaters to cool the heaters and adjacent wicks when the heaters have been deactivated.

Other aspects and advantages of the present application will become apparent upon consideration of the following detailed description and the attached drawings, in which like elements are assigned like reference numerals.

BRIEF DESCRIPTION OF THE DRAWINGS

FIG. 8 is a diagrammatic representation similar to that of FIG. 1 and illustrating a further embodiment of a volatile material diffuser;

FIG. 9 is a top elevational view of a further embodiment of a volatile material diffuser;

FIG. 30 is a graphical representation depicting temperature versus time for the diffuser of FIGS. 25-28 with a fan thereof turned on.

DETAILED DESCRIPTION

Figure 1:
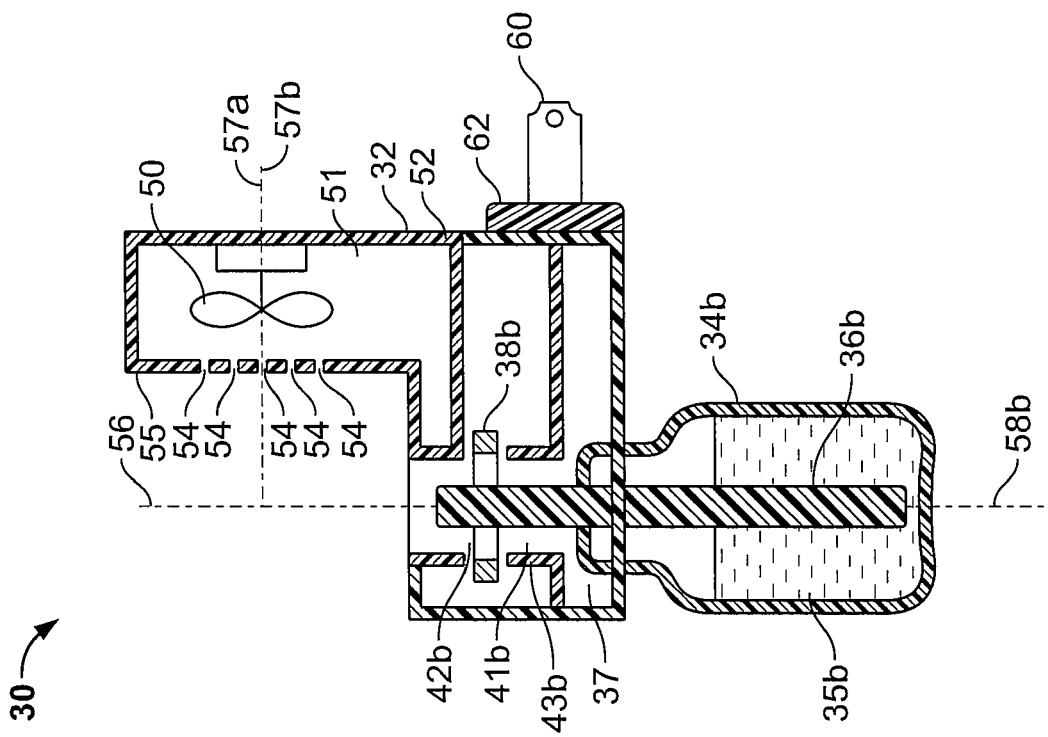
FIG. 1 is a diagrammatic representation of a first embodiment of a volatile material diffuser.
Figure 2:
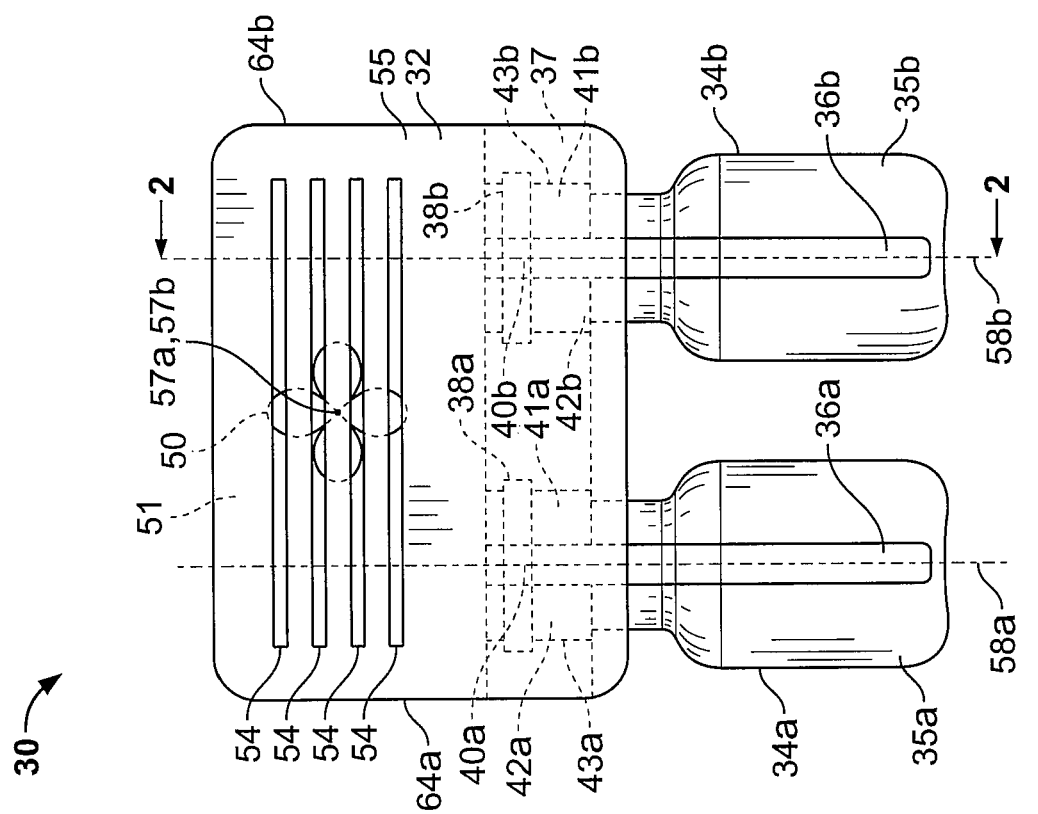
FIG. 2 is a cross-sectional view taken generally along the lines 2-2 of FIG. 1.

Referring to FIGS. 1 and 2, a volatile material diffuser 30 generally includes a housing 32. Two containers 34a, 34b having volatile materials 35a, 35b therein and wicks 36a, 36b in contact with the volatile materials 35a, 35b and extending out of the containers 34a, 34b are adapted to be inserted within the housing 32. The containers 34a, 34b may be inserted into and retained within the housing 32 by any means known in the art. For example, the containers 34a, 34b may include projections (not shown) on one or more surfaces thereof that fit into and are retained by grooves, ledges, or apertures in the housing 32. Such arrangements are described in detail in Wefler U.S. Design Pat. No. 393,063, Pedrotti et al. U.S. Pat. No. 6,862,403, and Duston et al. U.S. Pat. No. 7,032,831.

The volatile materials 35a, 35b within the containers 34a, 34b may be the same or different volatile materials 35a, 35b and also may of the same type or different types. The different types of volatile materials 35a, 35b that may be used include, for example, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Two volatile materials 35a, 35b of the same type need not be utilized. For example, an insecticide and a fragrance may be used, a disinfectant and a repellent may be used, or any other combination of types of volatile materials 35a, 35b may be used.

Referring again to FIGS. 1 and 2, the volatile material diffuser 30 a first chamber 37 including heaters 38a, 38b disposed adjacent the wicks 36a, 36b for vaporization of the volatile materials 35a, 35b, which move by capillary action through the wicks 36a, 36b to top portions 40a, 40b of the wicks 36a, 36b. The wicks 36a, 36b and heaters 38a, 38b reside within channels 41a, 41b (only 41b shown) formed within the first chamber 37. The channels 41a, 41b have a diameter that is greater than a diameter of the wicks 36a, 36b to provide a gap 42a, 42b (only 42b shown) between the wicks 36a, 36b and cylindrical walls 43a, 43b (only 43b shown) forming the respective channels 41a, 41b.

A fan 50 is disposed within a second chamber 51 in a rear portion 52 of the housing 32 and slots or vents 54 are disposed opposite the fan 50 in a front wall 55 forming the chamber 51. The fan 50 is disposed slightly above the wicks 36a, 36b and the heaters 38a, 38b along a vertical axis 56 of the diffuser 30. Referring to FIGS. 1 and 2, a longitudinal axis 57a of the fan 50 is coincident with a longitudinal axis 57b of the diffuser 30 and perpendicular to axes 58a, 58b of the wicks 36a, 36b, wherein the axes 58a, 58b of the wicks 36a, 36b are parallel to the vertical axis 56 of the diffuser 30. Air from the fan 50 is directed toward the vents 54 such that the air moves vaporized volatile material(s) 35a, 35b that are emitted from the wicks 36a, 36b away from the diffuser 30. The fan 50 also cools the wicks 36a, 36b and heaters 38a, 38b, as discussed in greater detail hereinafter.

Still referring to FIGS. 1 and 2, the diffuser 30 preferably, although not necessarily, has two electrical blades 60 (only one shown) extending from a rear side 62 thereof for insertion into a common electrical socket. In this manner, the diffuser 30 is supplied direct current to operate the heaters 38a, 38b and the fan 50. Optionally, the diffuser 30 may be battery-operated.

The diffuser 30 of FIGS. 1 and 2 operates in a manner that prevents habituation to a particular volatile material 35a, 35b, if a fragrance or the like is used. The diffuser 30 also limits the amount of mixing of two volatile materials 35a, 35b. In particular, the volatile materials 35a, 35b are emitted in an alternating sequence. When the diffuser 30 is plugged into an electrical socket, a first of the heaters 38a is activated to emit a first of the volatile materials 35a. After a first period of time, the first heater 38a is deactivated and a second of the heaters 38b is activated for a second period of time to emit a second of the volatile materials 35b. After the second period of time, the second heater 38b is deactivated, the first heater 38a is activated, and the sequence repeats until the diffuser 30 is unplugged from the electrical socket. In this sequence, the first and second heaters 38a, 38b are activated and deactivated simultaneously. Alternatively, a third period of time may elapse between deactivation of one of the heaters 38a, 38b and activation of the next heater 38a, 38b, thereby having no heater activated for the third period of time. Still alternatively, a fourth period of time may elapse between the activation of one of the heaters 38a, 38b and the deactivation of the other heater 38a, 38b, thereby creating an overlap of volatile materials 35a, 35b for the fourth period of time.

The first and second periods of time may be the same such that each heater 38a, 38b is activated for an equivalent period of time. Alternatively, the first and second periods of time may be different. The first and second periods of time may be between about 10 seconds and about 3 hours, more preferably between about 15 minutes and about 2 hours, and most preferably about 50 minutes or about 90 minutes.

When utilizing two volatile materials 35a, 35b, for example two fragrances, in the diffuser 30 of FIGS. 1 and 2, there is oftentimes an overlap of the emission of the volatile materials 35a, 35b despite the fact that the first heater 38a is deactivated before the second heater 38b is activated and the second heater 38b is deactivated before the first heater 38a is activated or the first and second heaters 38a, 38b are activated and deactivated at the same time. The reason for this is that it takes the deactivated heater 38a, 38b and the associated wick 36a, 36b a period of time to cool off. During this time of cooling off, the volatile material 35a, 35b associated with the deactivated heater 38a, 38b is still vaporized due to temperatures of the wicks 36a, 36b and the heaters 38a, 38b being quite a bit above ambient temperature and taking a long period of time to return to a steady state temperature. In addition, the steady state temperature may be enough above ambient that the presence of the volatile material 35a, 35b associated with a deactivated heater 38a, 38b may still be detected throughout the period when the heater 38a, 38b is deactivated. This overlap in emission of two volatile materials 35a, 35b is oftentimes undesirable because users may prefer to detect a single volatile material 35a, 35b and/or the volatile materials 35a, 35b are not compatible.

The fan 50 disposed within the diffuser 30 of the present disclosure provides a method of minimizing the overlap in emission of volatile materials 35a, 35b. In particular, air flow from the fan 50 flows through the vents 54 and over the channels 41a, 41b, thereby causing a chimney effect and allowing air to flow downwardly through the gaps 42a, 42b formed by the channels 41a, 41b. Air flow through the channels 41a, 41b cools the wicks 36a, 36b and heaters 38a, 38b. A testing protocol was established and followed to demonstrate the effectiveness of the fan 50 in minimizing overlap of emission of volatile materials 35a, 35b. The testing protocol was conducted on a multi-fragrancing diffuser similar to the diffuser 30 depicted in FIG. 1 and having two containers 34a, 34b each having wicks 36a, 36b extending therefrom and in contact with volatile materials 35a, 35b within the containers 34a, 34b. When the containers 34a, 34b are inserted into the diffuser 30, the top portions 40a, 40b of the wicks 36a, 36b are disposed within individual ring heaters 38a, 38b. A fan 50 is disposed above and behind the wicks 36a, 36b and heaters 38a, 38b as shown in FIG. 2. During all tests, the fan 50 was cycled between about 2000 and 2200 rotations per minute. First and second thermocouples were inserted into central portions of the first and second wicks 36a, 36b, respectively, coincident with axes 58a, 58b of the wicks 36a, 36b to measure a temperature of each of the wicks 38a, 38b during various points in time during the testing protocol.

Figure 3:
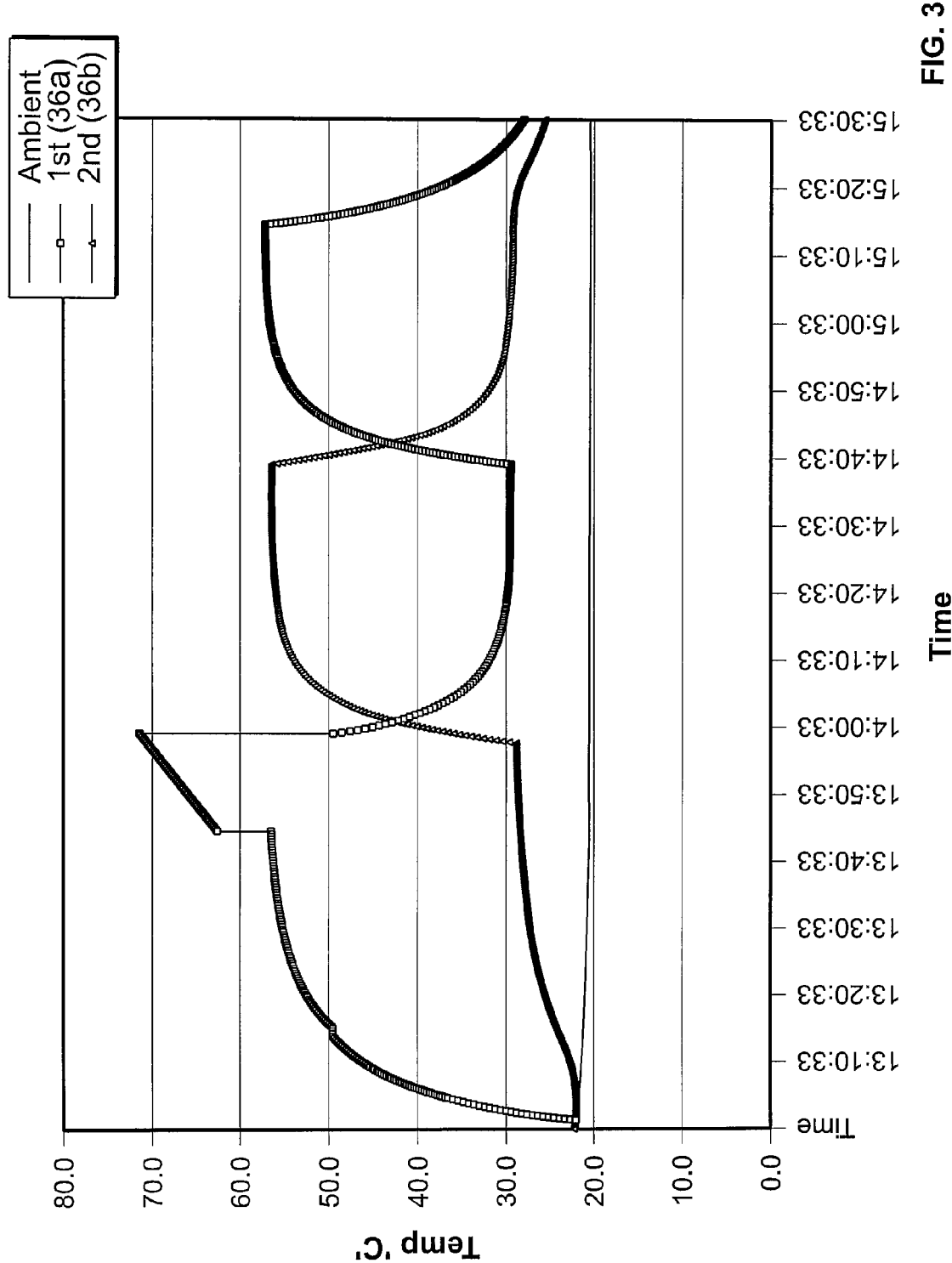
FIG. 3 is a graphical representation depicting temperature versus time for the diffuser of FIG. 1 with a fan turned off.

Referring to FIG. 3, the testing protocol first included a baseline test to show temperatures of the first and second wicks 36a, 36b with the fan turned off. The result was that, except for a jump in temperature from about time 13:45:00 to about time 14:00:00, each of the wicks 36a, 36b reached a maximum temperature of about 57 or 58 degrees Celsius (between about 135 or 136 degrees Fahrenheit) and each of the wicks 36a, 36b reached a minimum temperature of about 30 degrees Celsius (about 86 degrees Fahrenheit) with ambient temperature being about 21 degrees Celsius (about 70 degrees Fahrenheit). This baseline test shows that, even when a heater 38a, 38b is turned off, there is still residual heat within the associated wick 36a, 36b and/or heater 38a, 38b. This residual heat can be caused either by the inability of the wick 36a, 36b and/or heater 38a, 38b to cool quickly enough and/or the activated heater 38a, 38b transfers some heat to the wick 36a, 36b associated with the deactivated heater 38a, 38b. The jump in temperature as noted above was assumed to be an anomaly due to the start-up of the diffuser 30. This is supported in the fact that the jump did not occur again as the heaters 38a, 38b alternated.

Referring next to FIGS. 4-9, different positions for the fan 50 were tested to determine the most efficient positioning of the fan 50 with respect to cooling a deactivated wick 36a, 36b, but not cooling an activated wick 36a, 36b so much that emission of a corresponding volatile material 35a, 35b is not sufficient for the user.

Figure 4:
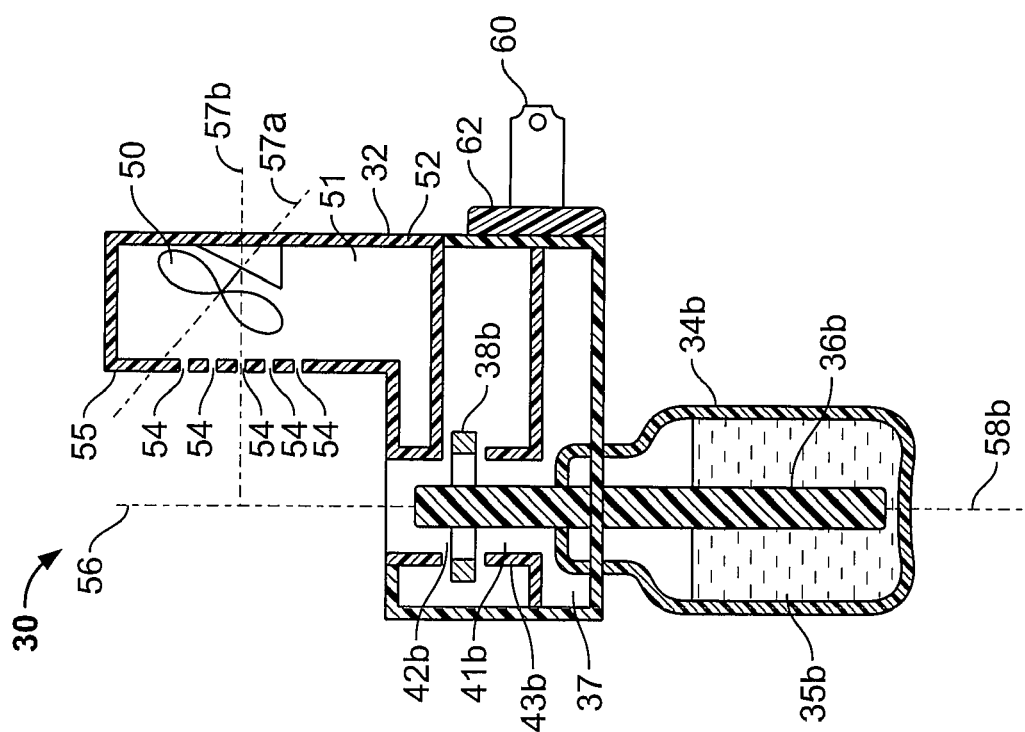
FIG. 4 is a diagrammatic representation similar to that of FIG. 1 and illustrating a second embodiment of a volatile material diffuser.
Figure 5:
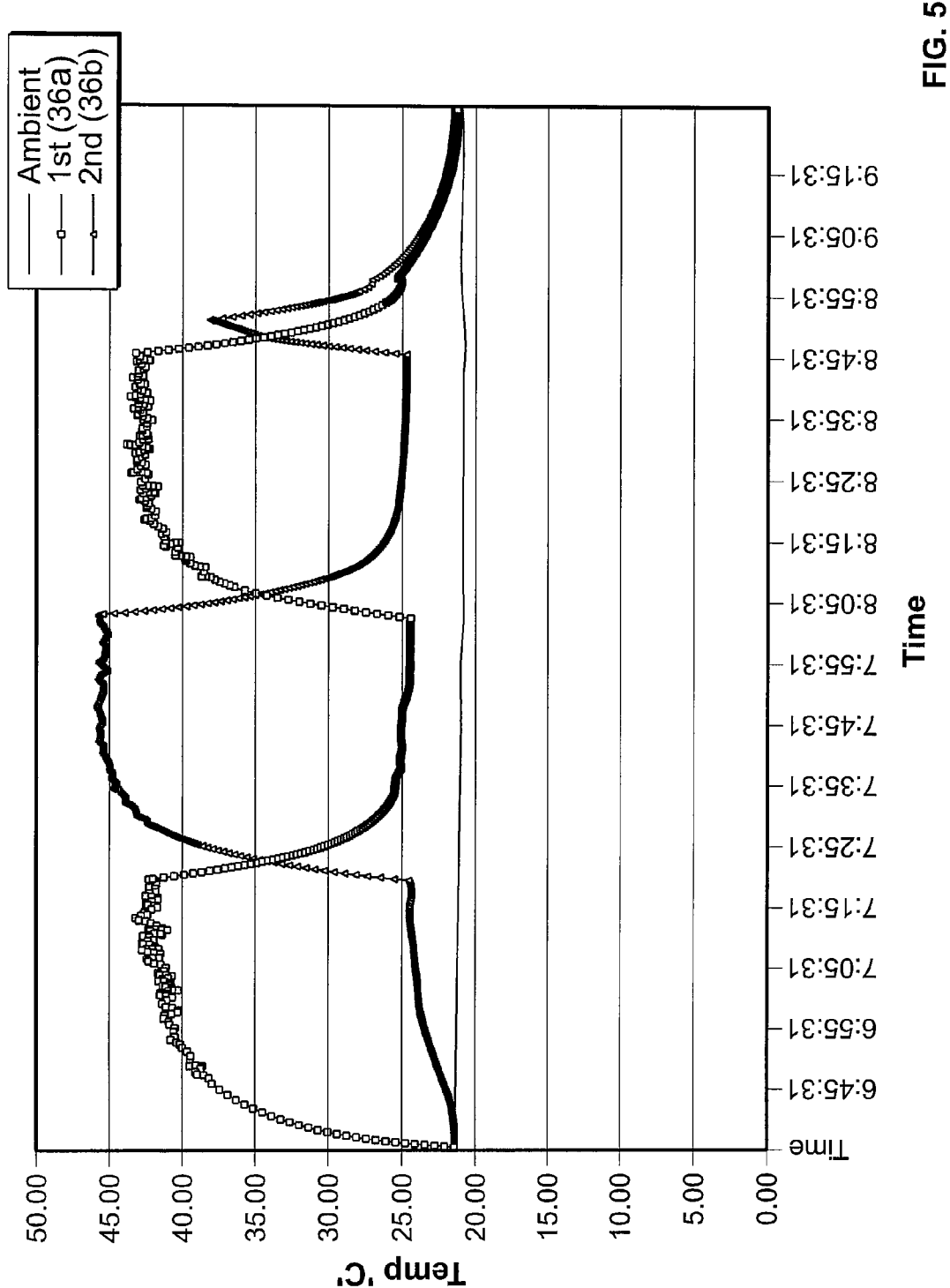
FIG. 5 is a graphical representation depicting temperature versus time for the diffuser of FIG. 4.

As seen in FIG. 4, the fan 50 is angled upwardly at an angle of about 45 degrees with respect to the longitudinal axis 57b of the diffuser 30. In the embodiments herein in which the fan 50 is angled, the fan 50 is further directed toward a center point between axes 58a, 58b of the wicks 36a, 36b such that an equal amount of airflow is directed toward each wick 36a, 36b. During a period of testing, as seen in FIG. 5, the wicks 36a, 36b reached a maximum temperature of between about 43 and about 45 degrees Celsius (between about 109 and 113 degrees Fahrenheit) and each of the wicks 36a, 36b reached a minimum temperature of about 25 degrees Celsius (about 77 degrees Fahrenheit) with ambient temperature still being about 21 degrees Celsius (about 70 degrees Fahrenheit). As is evident from the data of FIG. 5, both the minimum and maximum temperatures of the wicks 36a, 36b are less than the minimum and maximum temperatures of the wicks 36a, 36b with no fan 50, as seen in FIG. 3. During deactivation of a heater 38a, 38b, the associated wick 36a, 36b generally cooled enough that the associated volatile material 35a, 35b would not be perceived by most users.

Figure 6:
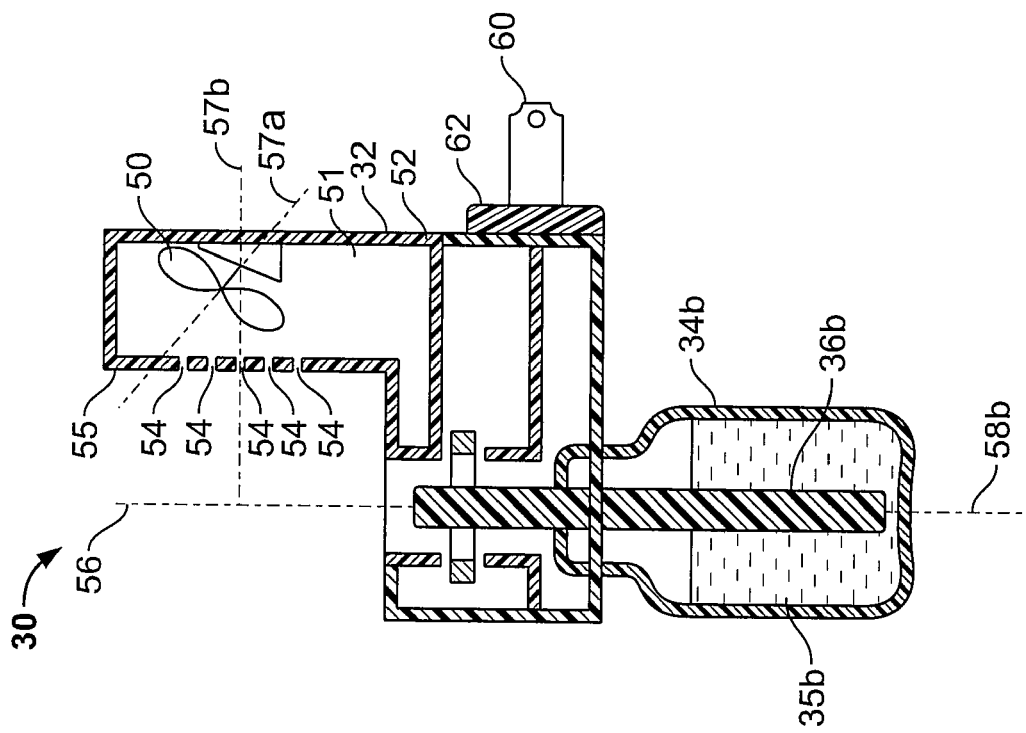
FIG. 6 is a diagrammatic representation similar to that of FIG. 1 and depicting a third embodiment of a volatile material diffuser.
Figure 7:
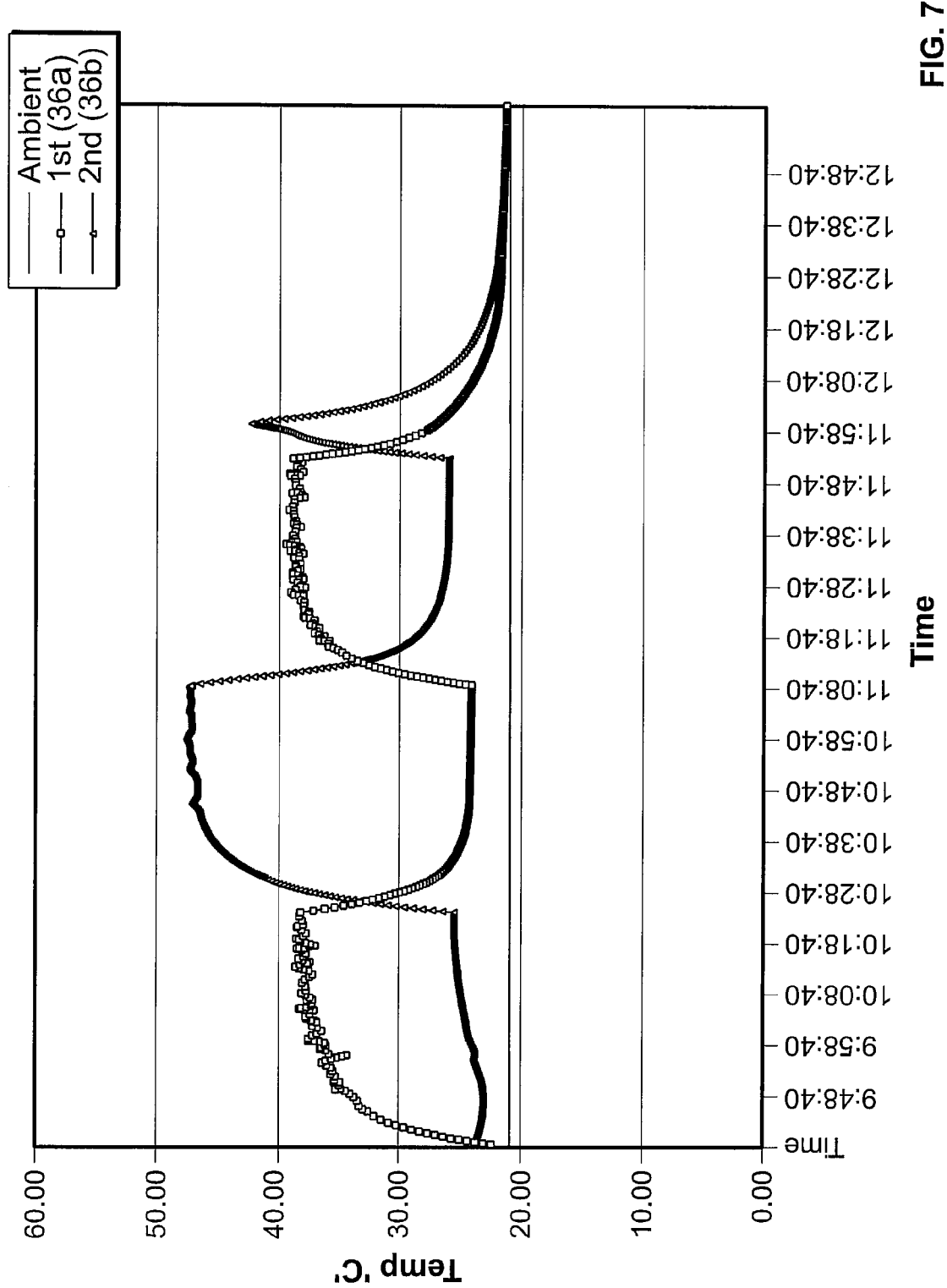
FIG. 7 is a graphical representation depicting temperature versus time for the diffuser of FIG. 6.

Referring now to FIG. 6, the fan 50 is angled upwardly at an angle of about 22.5 degrees with respect to the longitudinal axis 57b of the diffuser 30. During a period of testing, as seen in FIG. 7, the wicks 36a, 36b reached a maximum temperature of between about 38 and about 48 degrees Celsius (between about 100 and about 118 degrees Fahrenheit) and each of the wicks 36a, 36b reached a minimum temperature of between about 24 and about 26 degrees Celsius (between about 75 and about 79 degrees Fahrenheit) with ambient again being about 21 degrees Celsius (about 70 degrees Fahrenheit). Again, the data of FIG. 7 shows that the fan 50 cools the wicks 36a, 36b and/or heaters 38a, 38b when the heaters 38a, 38b are activated and deactivated. The key is to find an angle at which the wick 36a, 36b associated with the activated heater 38a, 38b is not cooled too much as to decrease a user's enjoyment of the diffuser 30, but where the angle is such that the wick 36a, 36b associated with the deactivated heater 38a, 38b is cooled enough such that most users generally cannot perceive the volatile material 35a, 35b associated with the deactivated heater 38a, 38b.

Other fan 50 orientations are depicted in FIGS. 1 and 8. In FIG. 1, discussed in detail above, the fan 50 is not angled upwardly or downwardly at all (at zero degrees) with respect to the longitudinal axis 57b of the diffuser 30. FIG. 8 depicts the fan 50 angled downwardly about 5 degrees with respect to the longitudinal axis 57b of the diffuser 30.

Although a set number of vents 54 is depicted in the embodiments herein, any number of vents 54 may be utilized in any of the embodiments herein.

Although the fans 50 herein are shown angled upwardly at 45 degrees with respect to the longitudinal axis 57b of the diffuser 30, upwardly at 22.5 degrees with respect to the longitudinal axis 57b, at zero degrees with respect to the longitudinal axis 57b, and downwardly at 5 degrees with respect to the longitudinal axis 57b, other angles are possible. Specifically, any angle disposed between a downward angle of about 45 degrees and an upward angle of about 45 degrees with respect to the longitudinal axis 57b of the diffuser 30 is possible.

Figure 10:
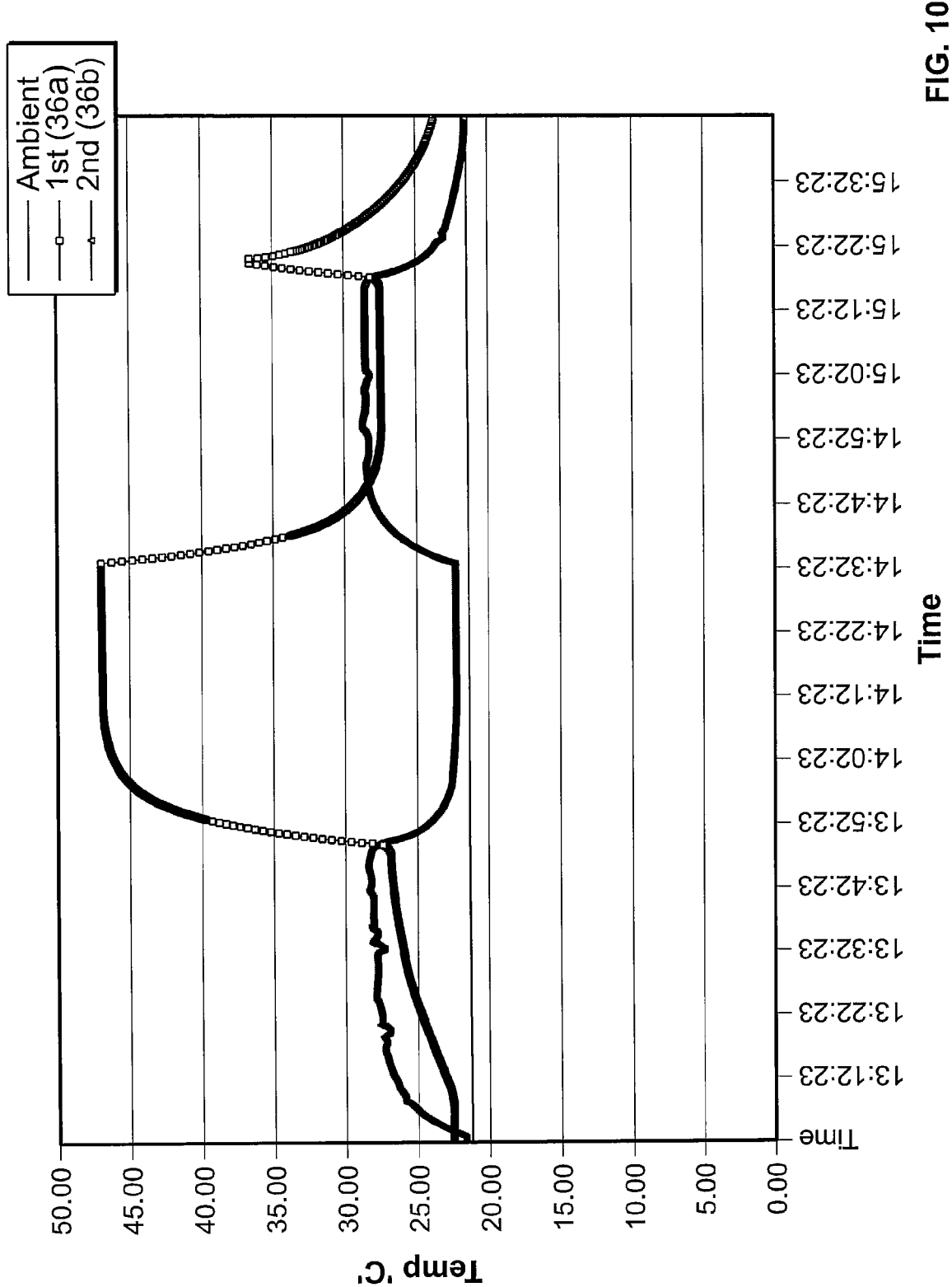
FIGS. 10 and 11 are graphical representations depicting temperature versus time for two variations of the diffuser of FIG. 9.

The fan 50 of any of the embodiments herein may be angled toward a side wall 64a, 64b of the housing 32 with respect to a longitudinal axis 57b of the diffuser 30, as seen in FIG. 9, if it is desired to cool one of the wicks 36a, 36b more than the other. In particular, the fan 50 may be angled toward either side wall 64a, 64b at an angle of between about 0 and about 45 degrees with respect to the longitudinal axis 57b. Referring to the same testing protocol as described above, in FIG. 10, the fan 50 was not angled upwardly or downwardly (at zero degrees) with respect to the longitudinal axis 57b (FIG. 1) and was angled toward the second wick 36b, as seen in FIG. 9. As seen in FIG. 10, the second wick 36b is cooled much more than the first wick 36a. In fact, the second wick 36b has a maximum temperature of about 28 degrees Celsius (about 82 degrees Fahrenheit) and a minimum temperature of about 23 degrees Celsius (about 73 degrees Fahrenheit), with ambient temperature being about 21 degrees Celsius (about 70 degrees Fahrenheit). The first wick 36a has a maximum temperature of about 47 degrees Celsius (about 117 degrees Fahrenheit) and a minimum temperature of about 27 degrees Celsius (about 81 degrees Fahrenheit).

Figure 11:
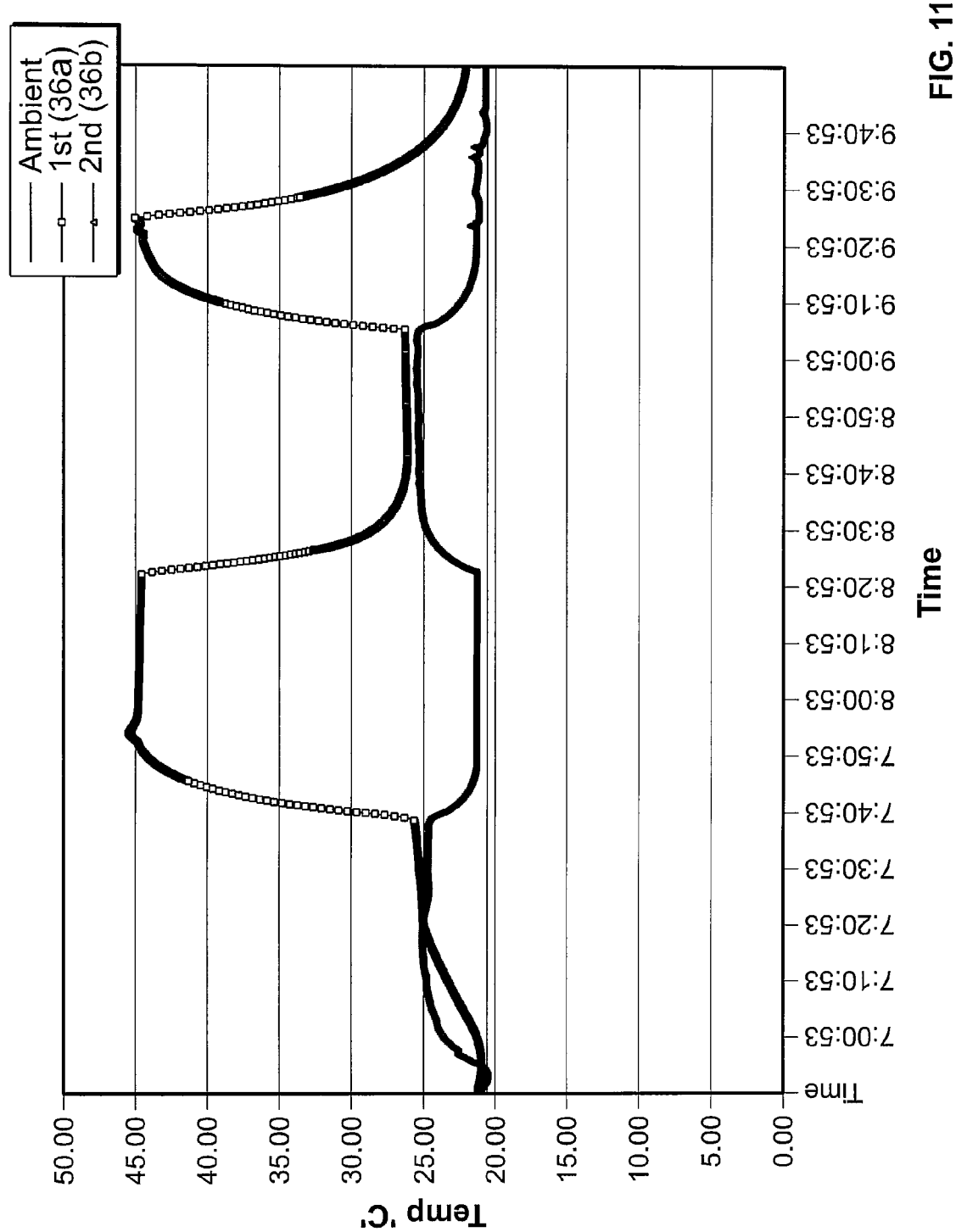

For the results of FIG. 11, a diffuser 30 was utilized wherein the fan 50 was angled downwardly at angle of 5 degrees with respect to the longitudinal axis 57b of the diffuser 30 (FIG. 8) and angled toward the second wick 36b, as seen in FIG. 9. The result was a maximum temperature for the first wick 36a of about 45 degrees Celsius (about 113 degrees Fahrenheit) and minimum temperature of about 27 degrees Celsius (about 81 degrees Fahrenheit). The second wick 36b had a maximum temperature of about 26 degrees Celsius (about 79 degrees Fahrenheit) and a minimum temperature of about 22 degrees Celsius (about 72 degrees Fahrenheit), with ambient again at about 21 degrees Celsius (about 70 degrees Fahrenheit).

Although the fan 50 is shown angled toward the second wick 36b with respect to the longitudinal axis 57b in FIG. 9, the fan 50 could also be angled toward the first wick 36a. The goal in the embodiments of FIGS. 9-11 is to cool one wick 36a, 36b at a much faster rate than the other wick 36a, 36b and/or to provide much less heat overall to one wick 36a, 36b than the other wick 36a, 36b. This may be desired when two different types of volatile materials 35a, 35b are utilized or there is simply a desire to emit one volatile material 35a, 35b less than another.

Figure 12:
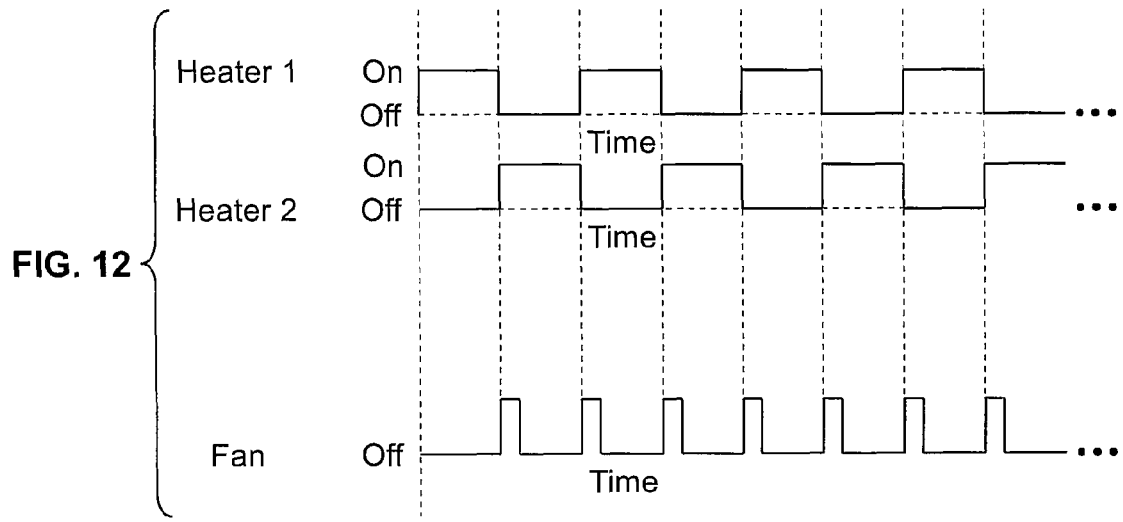
FIG. 12 is a diagrammatic representation of a mode of operation for heaters and a fan of any of the volatile material diffusers of FIGS. 1, 4, 6, and 8.

The fan 50 may be operated such that energy is continuously supplied to the fan 50, thus the fan 50 supplies a continuous air flow. The fan 50 may also be operated at a single speed, wherein the speed is not altered during the sequence, as described above. Alternatively, energy may be supplied intermittently to the fan 50 to create intermittent flows of air. Such a mode of operation is depicted in FIG. 12. FIG. 12 depicts first and second heaters 38a, 38b that are activated and deactivated at the same time throughout the alternating sequence. Energy is supplied to the fan 50 for a fifth period of time after the deactivation of each heater 38a, 38b, as further depicted in FIG. 12. The fifth period of time is between about 30 seconds and about 5 minutes depending on a speed of air flow from the fan 50, an angle of the fan 50, and a temperature of the surrounding air.

Figure 13:
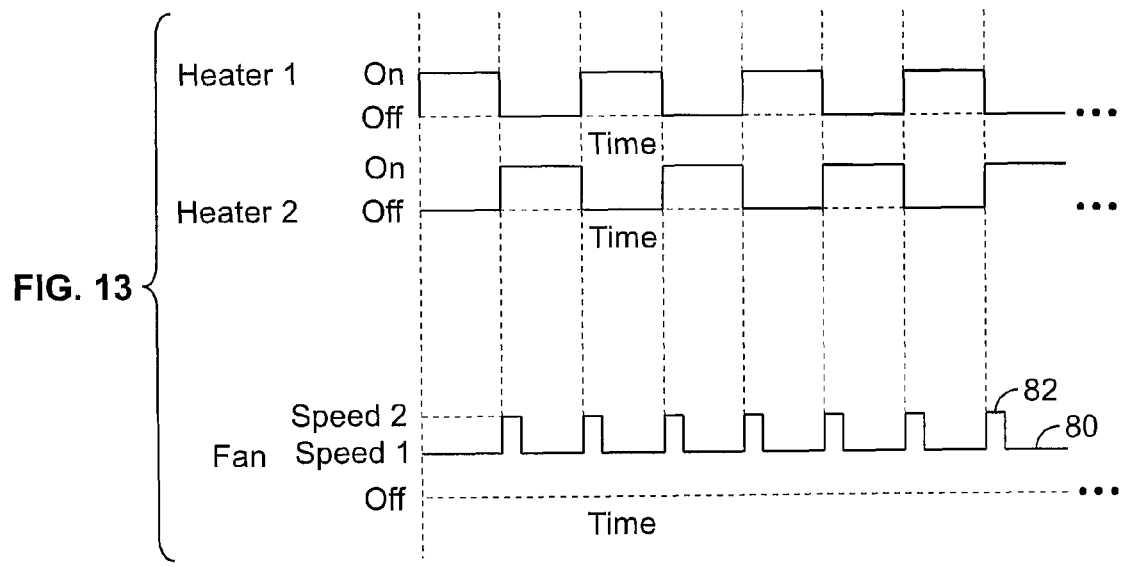
FIG. 13 is a diagrammatic representation of a mode of operation for heaters and a fan of any of the volatile material diffusers of FIGS. 1, 4, 6, and 8.

In another embodiment, as depicted in FIG. 13, the heaters 38a, 38b are energized in the same fashion as in FIG. 12, but the fan 50 is continuously energized. In this mode of operation, a speed of the fan 50 is alternated between a first speed 80 and a second speed 82. The fan 50 is energized to run at the second speed 82 immediately after deactivation of a heater 38a, 38b for the fifth time period and the rest of the time, the fan 50 is energized to run at the first speed 80. The first and second speeds 80, 82 are different from one another, the second speed 82 is preferably greater than the first speed 80, and both speeds are greater than zero rotations per minute in this embodiment. The second speed 82 being greater than the first speed 80 not only provides cooling for the wicks 36a, 36b immediately after deactivation of a corresponding heater 38a, 38b, but also simultaneously provides a burst of the volatile material 35a, 35b corresponding to the activated heater 38a, 38b. The first speed 80 being less than the second speed 82 also modulates the amount of volatile material 35a, 35b that is emitted such that bursts of the volatile materials 35a, 35b aid in minimizing habituation.

Figure 14:
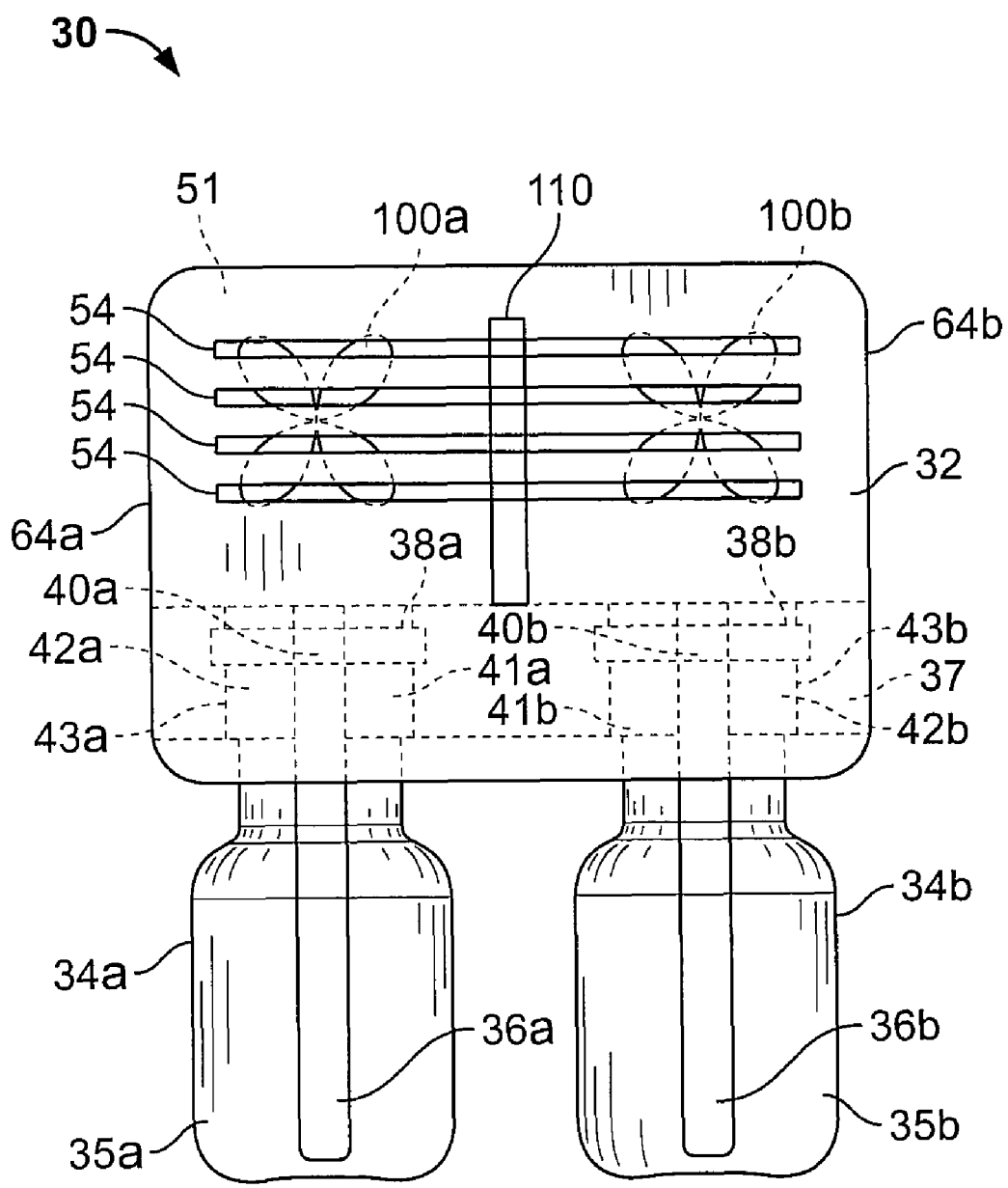
FIG. 14 is a diagrammatic representation of another embodiment of a volatile material diffuser.
Figure 15:
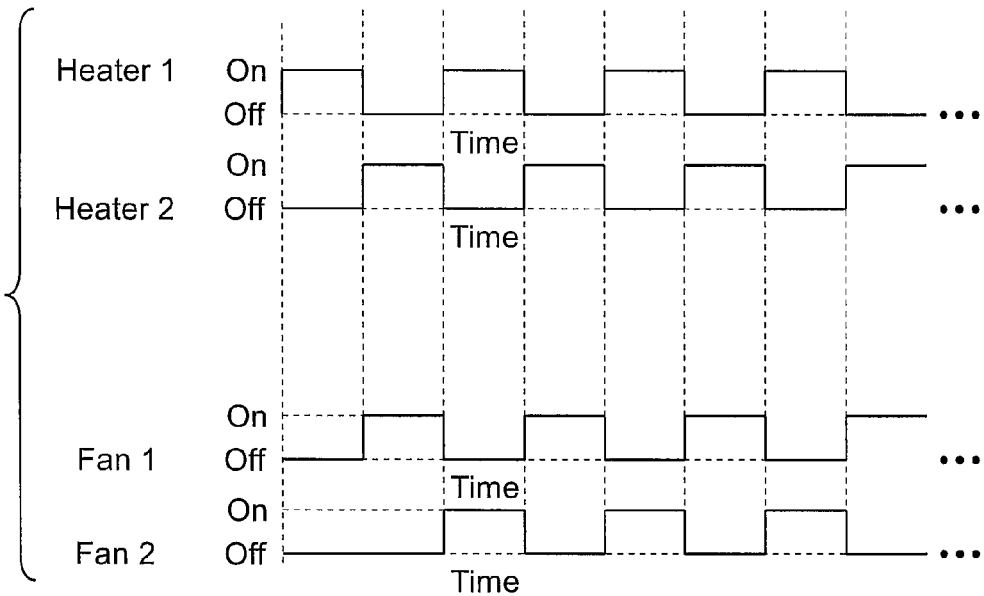
FIGS. 15 and 16 are diagrammatic representations of different modes of operation for heaters and fans of the volatile material diffuser of FIG. 11.
Figure 16:
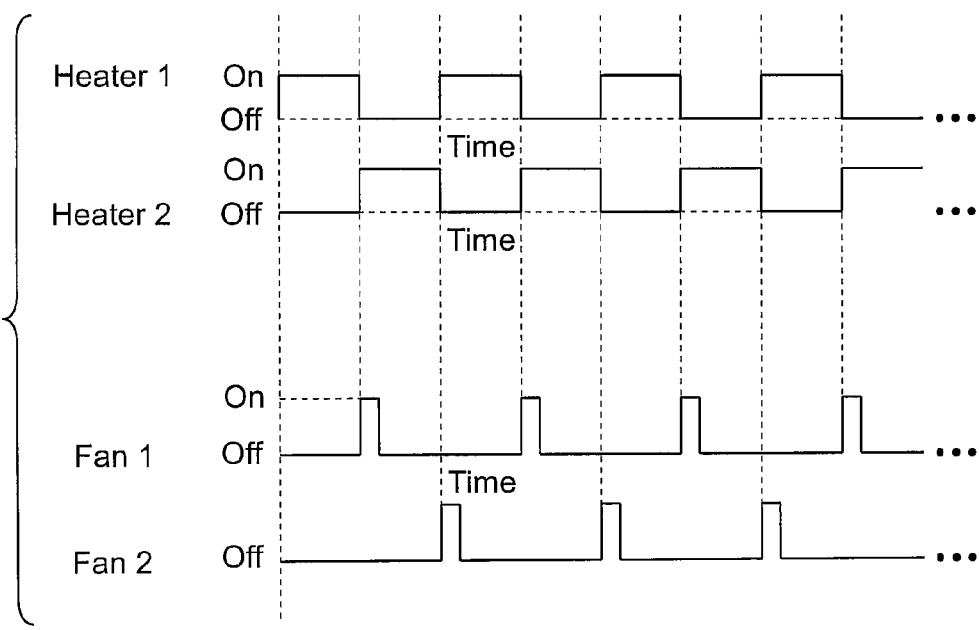

Referring to FIGS. 14-16, two fans 100a, 100b can alternatively be used in place of the single fan 50. Referring to FIG. 14, each of the fans 100a, 100b is aligned with a single wick 36a, 36b and a single heater 38a, 38b, respectively. The heaters 38a, 38b may be energized in any fashion as described herein. As an example mode of operation for the fans 100a, 100b and referring to FIGS. 15 and 16, the heaters 38a, 38b are alternated similarly to the manner in which the heaters 38a, 38b are alternated in FIGS. 12 and 13. The fans 100a, 100b are also automatically alternated such that the fan 100a, 100b associated with a heater 38a, 38b is activated when the associated heater 38a, 38b is deactivated. In FIG. 15, the fans 100a, 100b are shown as being activated for the entire period that the associated heater 38a, 38b is deactivated, whereas in FIG. 16, the fans 100a, 100b are only activated for the fifth period of time when the associated heater is deactivated.

The sample graphical depictions of modes of operation of FIGS. 12, 13, 15, and 16 depicting activation and deactivation of the heaters 38a, 38b and fans 50 or 100a, 100b are meant to show examples of activation and deactivation of same and are not meant to be limiting. In particular, the heaters 38a, 38b may be alternated in any fashion, as described in detail above.

Referring again to FIG. 14, a shield 110 in the form of a wall or other blocking structure is disposed external to the second chamber 51 between the first and second fans 100a, 100b so as to block air flow from the first fan 100a to the second wick 36b and the second heater 38b and block air flow from the second fan 100b to the first wick 36a and the first heater 38a.

Figure 18:
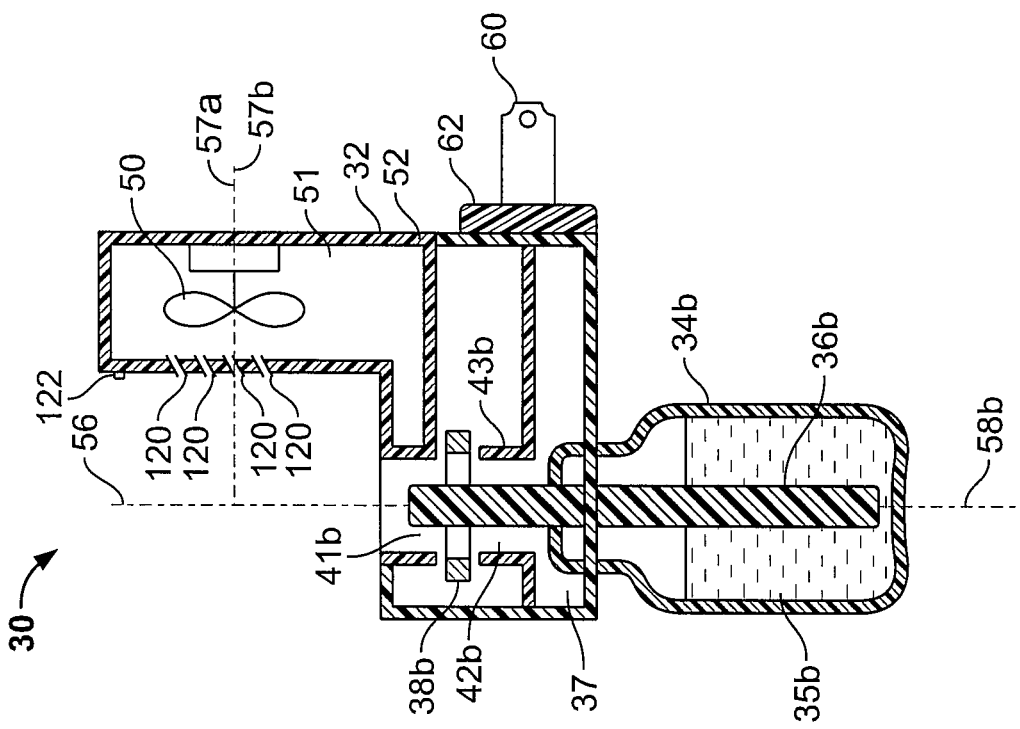
FIGS. 17 and 18 are diagrammatic representations similar to that of FIG. 1 of a further embodiment of a volatile material diffuser.
Figure 17:
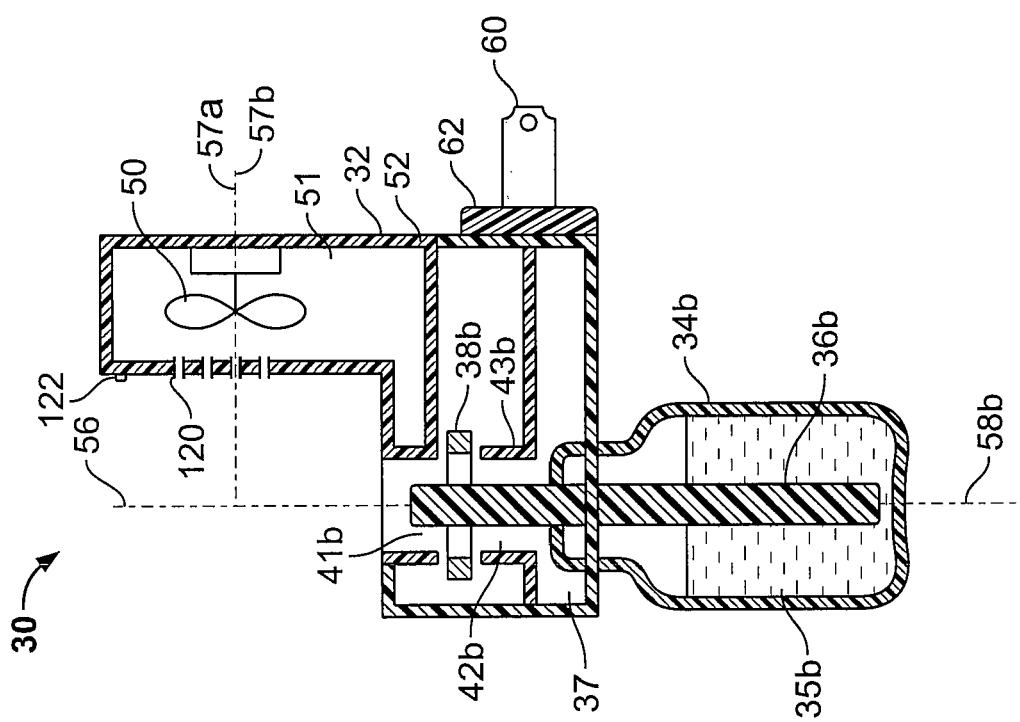

Referring to FIGS. 17 and 18, a set of louvers 120 may replace the vents 54, as discussed herein. The louvers 120 are shown in FIG. 17 as parallel to the axis 57a of the fan 50. An adjustment mechanism 122 may be placed on the housing 32 to allow a user to adjust the louvers 120. As such, the louvers 120 may be moved to any angle between a downward angle of about 45 degrees with respect to the longitudinal axis 57b of the diffuser 30 and an upward angle of about 45 degrees with respect to the longitudinal axis 57b. FIG. 18 depicts the louvers 120 in an adjusted position having a downward angle of about 30 degrees. Although louvers 120 are shown in FIG. 17 as directing air flow, any means by which air flow can be directed may be utilized.

Figure 19:
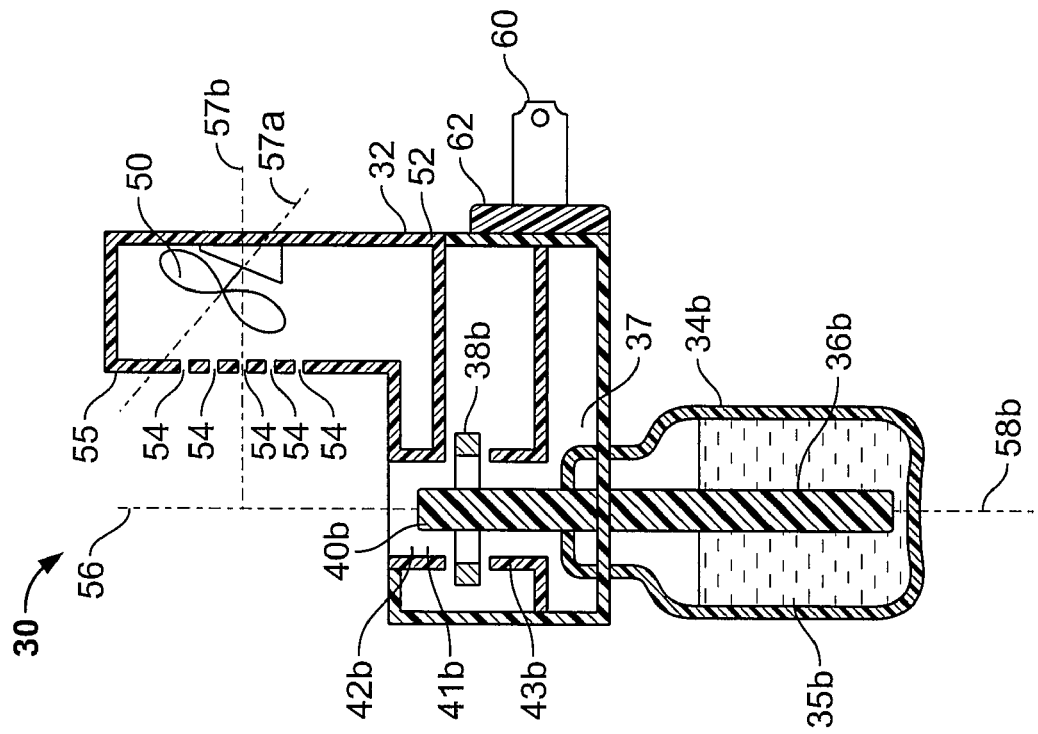
FIGS. 19-21 are diagrammatic representations of further embodiments of volatile material diffusers.
Figure 20:
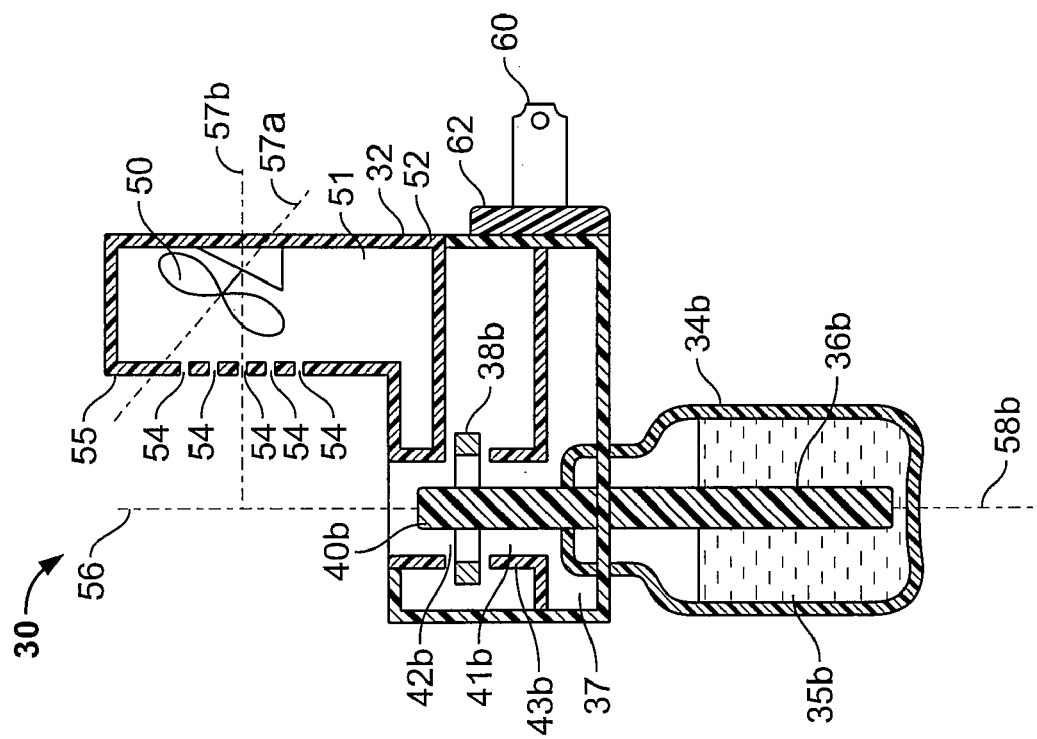
Figure 21:
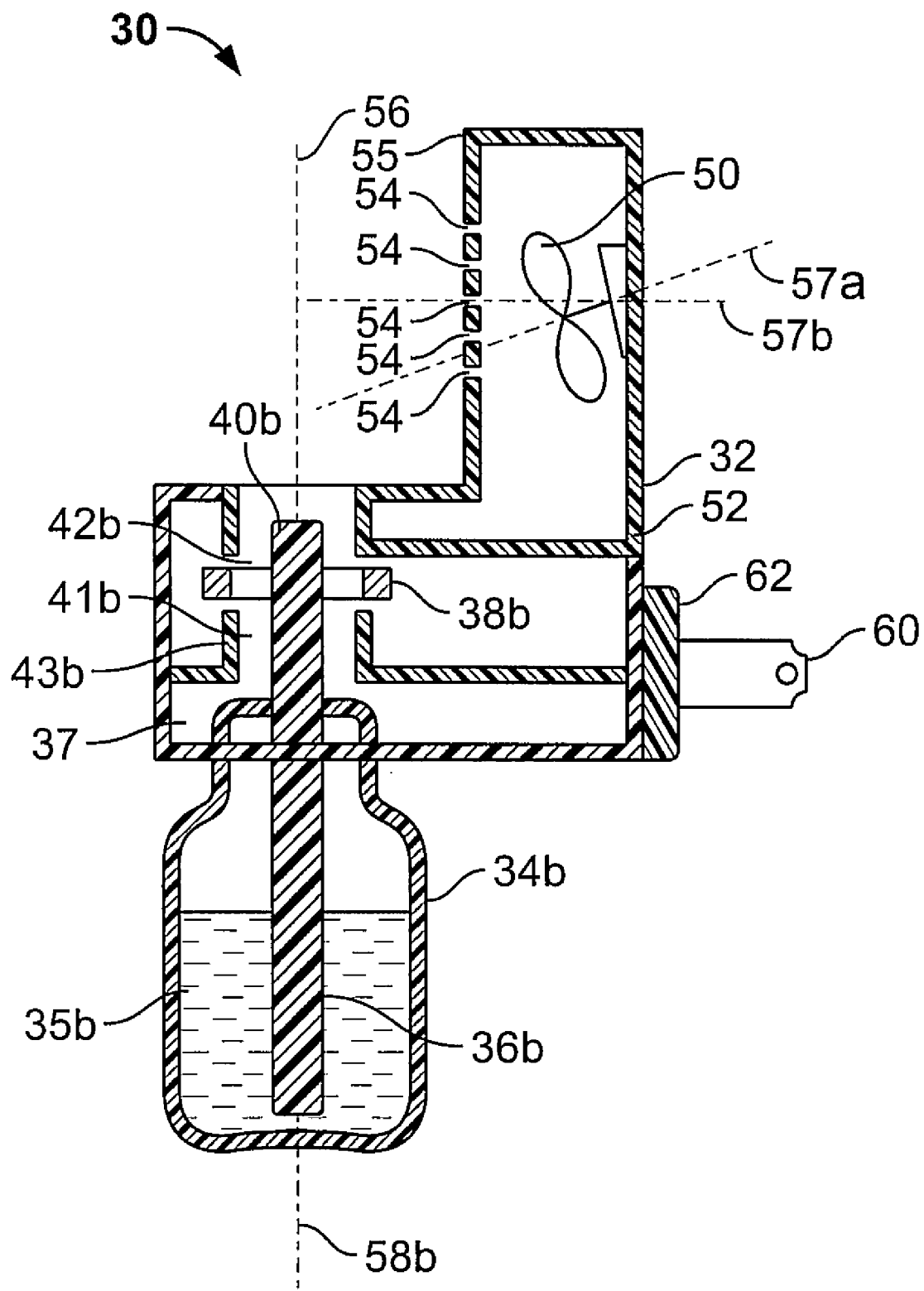
Figure 22:
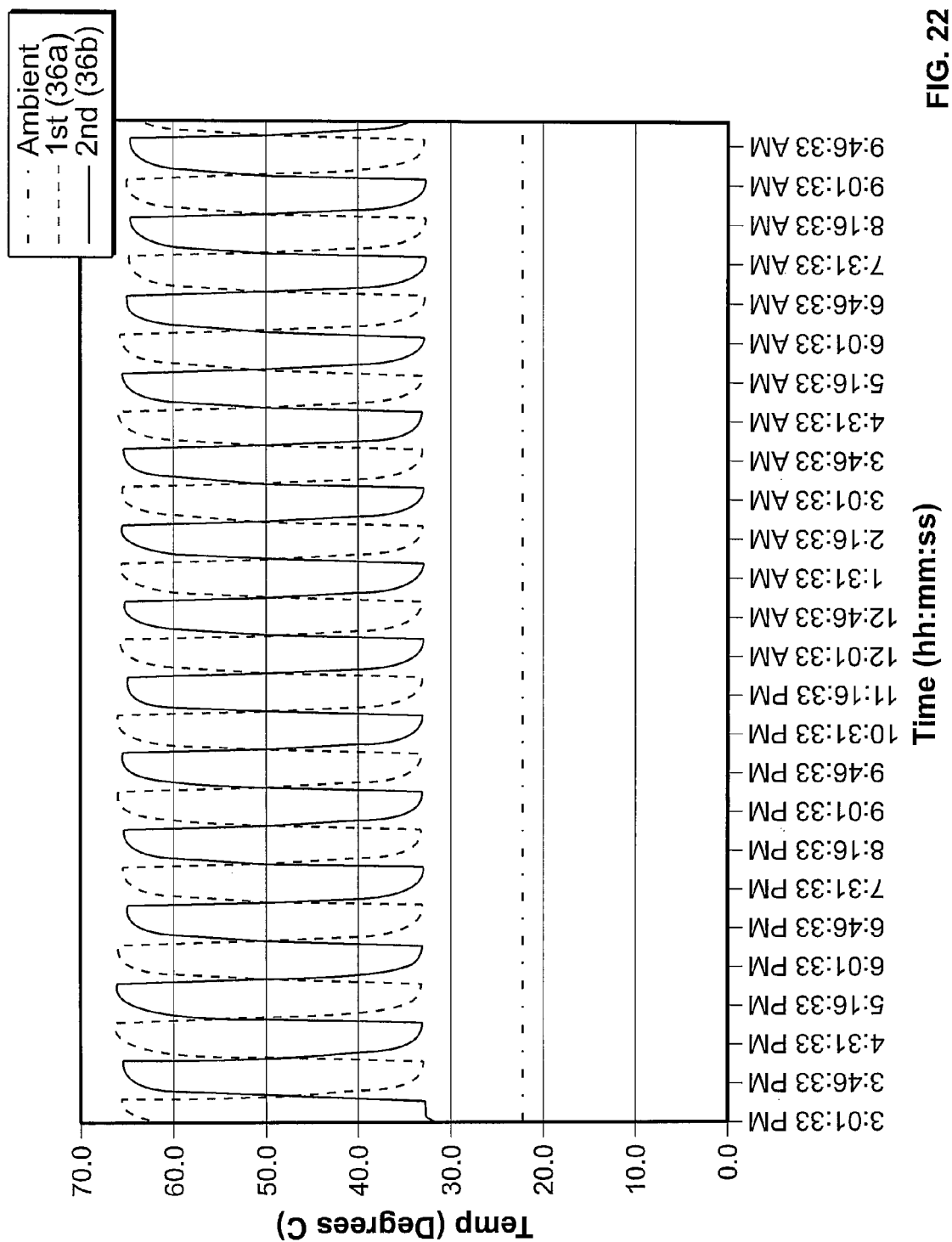
FIGS. 22-24 are graphical representations depicting temperature versus time for the diffusers of FIGS. 19-21, respectively.
Figure 23:
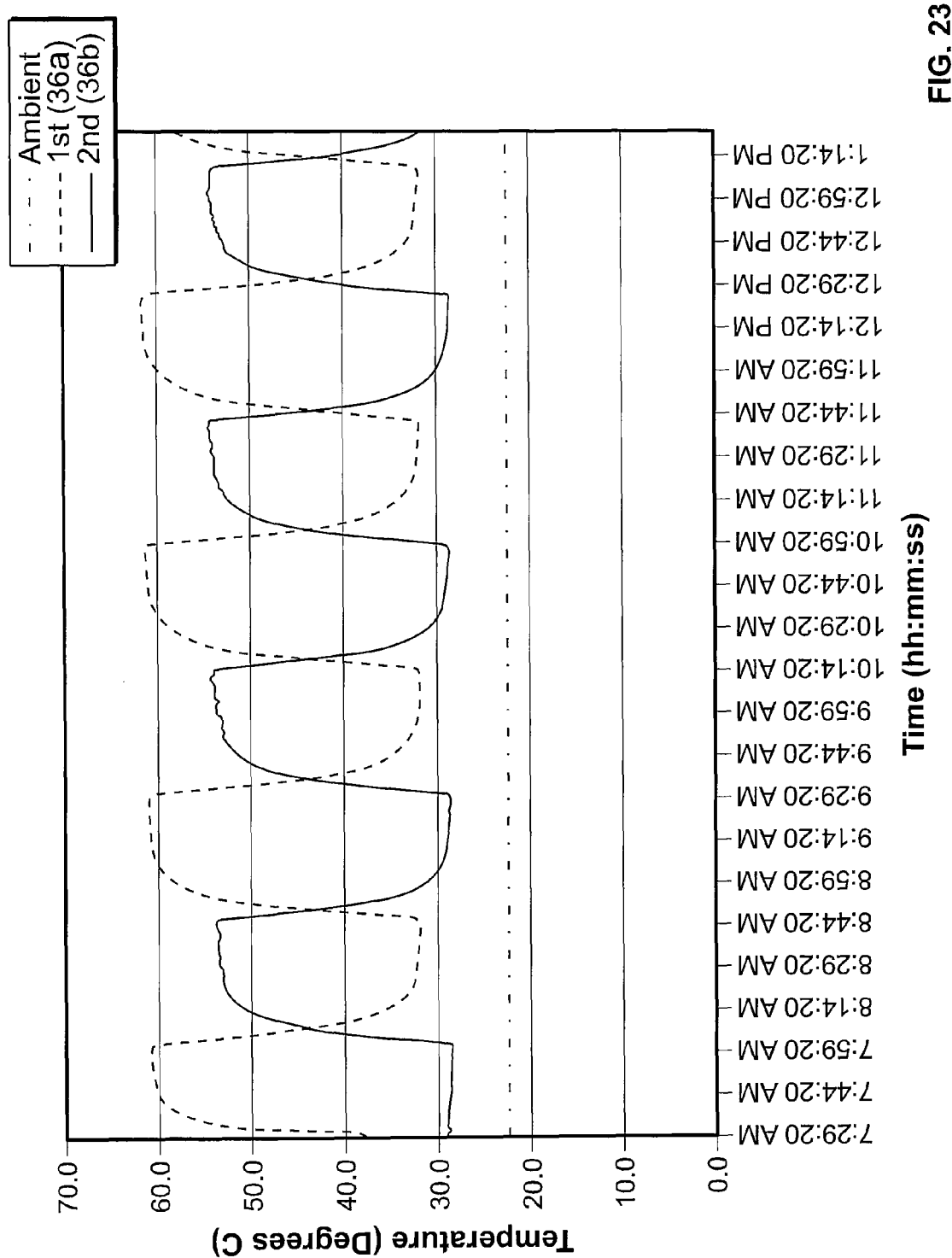
Figure 24:
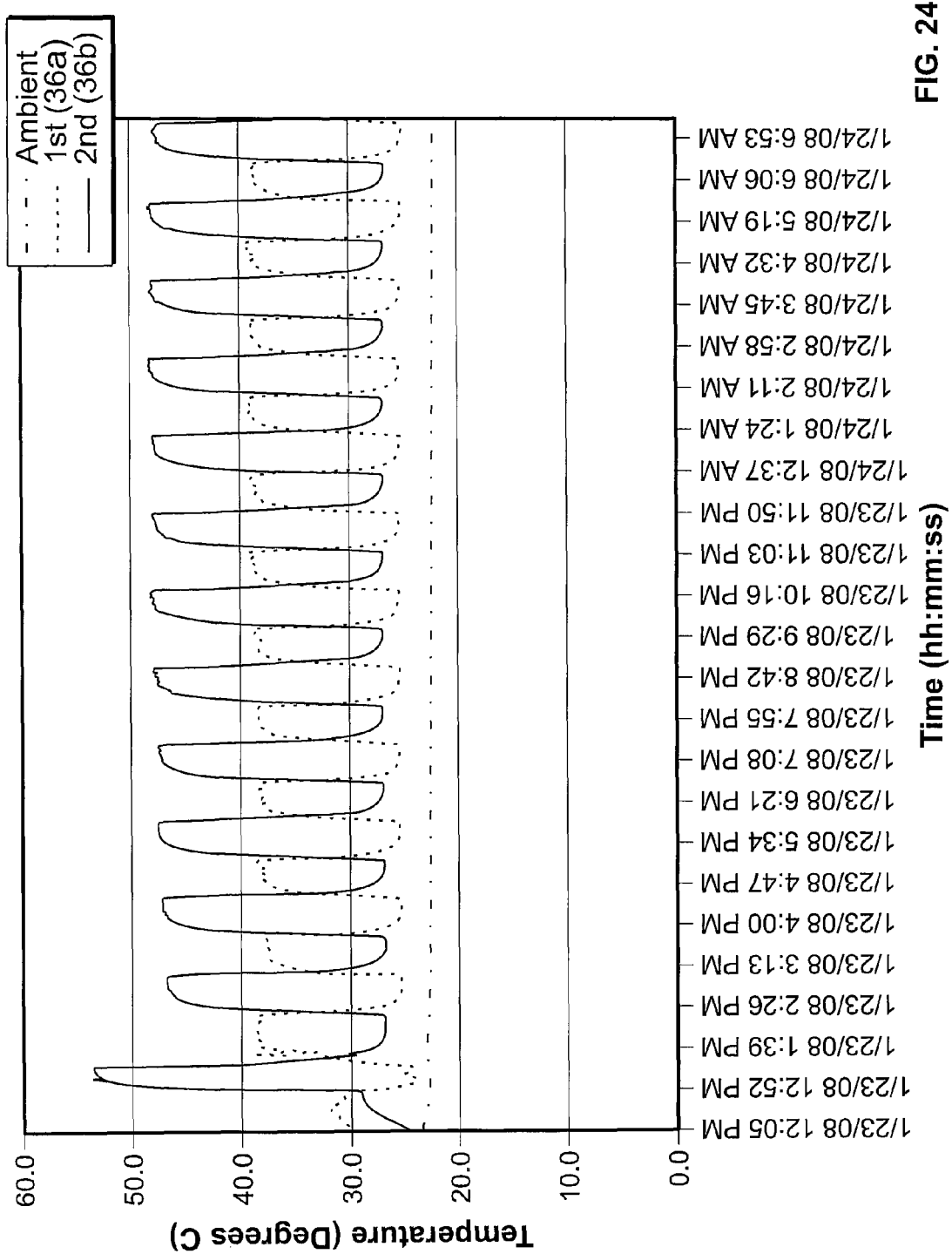

Another independent set of tests was conducted on the volatile material diffusers 30 depicted in FIGS. 19-21, wherein such diffusers 30 are similar to the diffusers 30 of FIGS. 2, 4, 6, and 8, except in the angling of the fan 50. In addition, the same testing protocol as described above was utilized. In FIGS. 19-21, the fan 50 is angled at 36 degrees, 21 degrees, and −9 degrees with respect to the longitudinal axis 57b of the diffuser 30, respectively. Each diffuser 30 of FIGS. 19-21 was tested for a period of time and the results were recorded in FIGS. 22-24, respectively. Referring to FIG. 22, which depicts testing with the fan 50 angled at about 36 degrees with respect to the longitudinal axis 57b, the wicks 36a, 36b reached a maximum temperature of between about 64 and about 66 degrees Celsius (between about 147 and about 151 degrees Fahrenheit) and each of the wicks 36a, 36b reached a minimum temperature of about 33 degrees Celsius (about 91 degrees Fahrenheit). FIG. 23 represents test results from the diffuser 30 of FIG. 20, wherein the fan 50 is angled at about 21 degrees with respect to the longitudinal axis 57b. In such test, the wicks 36a, 36b reached a maximum temperature of between about 53 and about 61 degrees Celsius (between about 127 and about 142 degrees Fahrenheit) and the wicks 36a, 36b reached a minimum temperature of between about 28 and about 32 degrees Celsius (between about 82 and about 90 degrees Fahrenheit). Referring next to FIG. 24, wherein a test was performed with the fan 50 angled at about −9 degrees with respect to the longitudinal axis 57b, the wicks 36a, 36b reached a maximum temperature of between about 47 and about 57 degrees Celsius (between about 117 and about 135 degrees Fahrenheit) and the wicks 36a, 36b reached a minimum temperature of between about 25 and about 27 degrees Celsius (between about 77 and about 81 degrees Fahrenheit). In all three tests of FIGS. 19-24, ambient temperature measured about 22 or 23 degrees with ambient about 22 degrees Celsius (about 72 or about 73 degrees Fahrenheit). As with the other test results described herein, it is evident that the angle at which the fan 50 is disposed with respect to the longitudinal axis 57b affects the rate at which the wicks 36a, 36b and/or heaters 38a, 38b are cooled.

Figure 26:
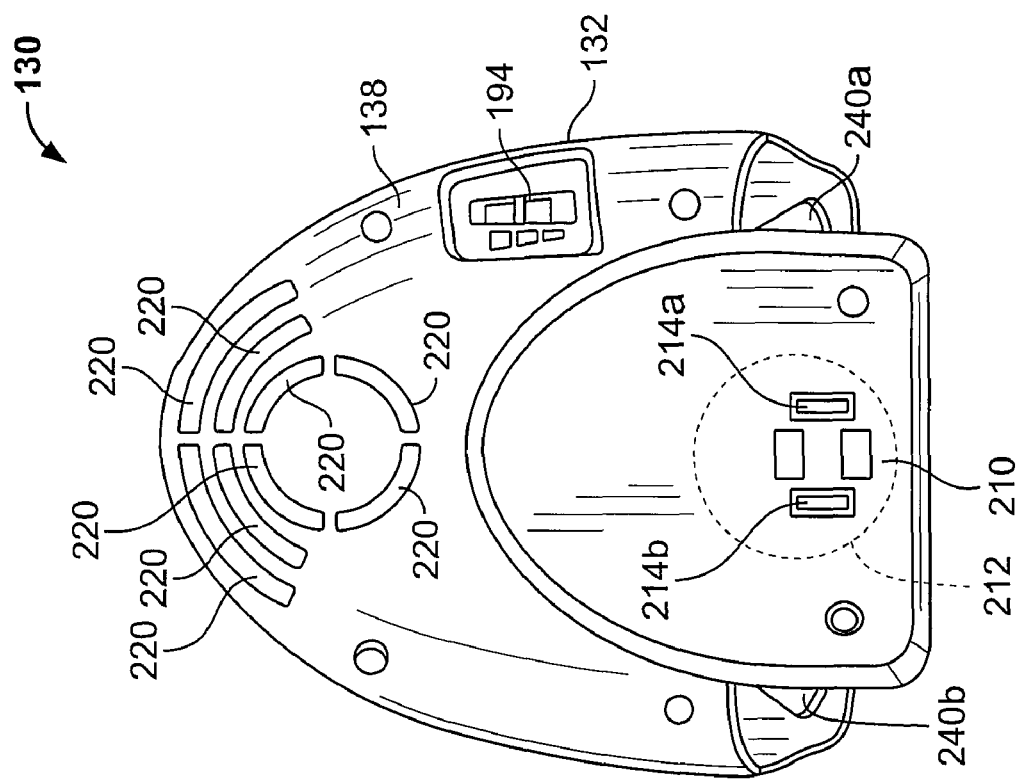
FIGS. 26 and 27 are rear and front elevational views, respectively, of the diffuser of FIG. 25.
Figure 25:
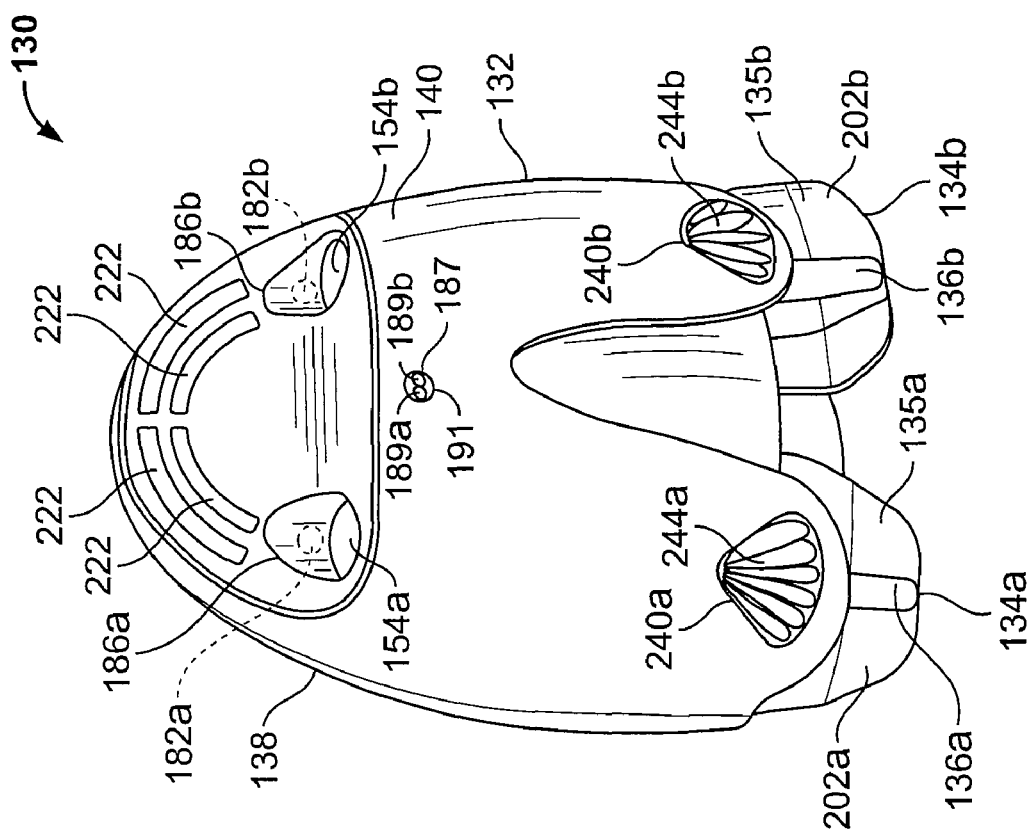
FIG. 25 is a front isometric view of a further embodiment of a volatile material diffuser.
Figure 27:
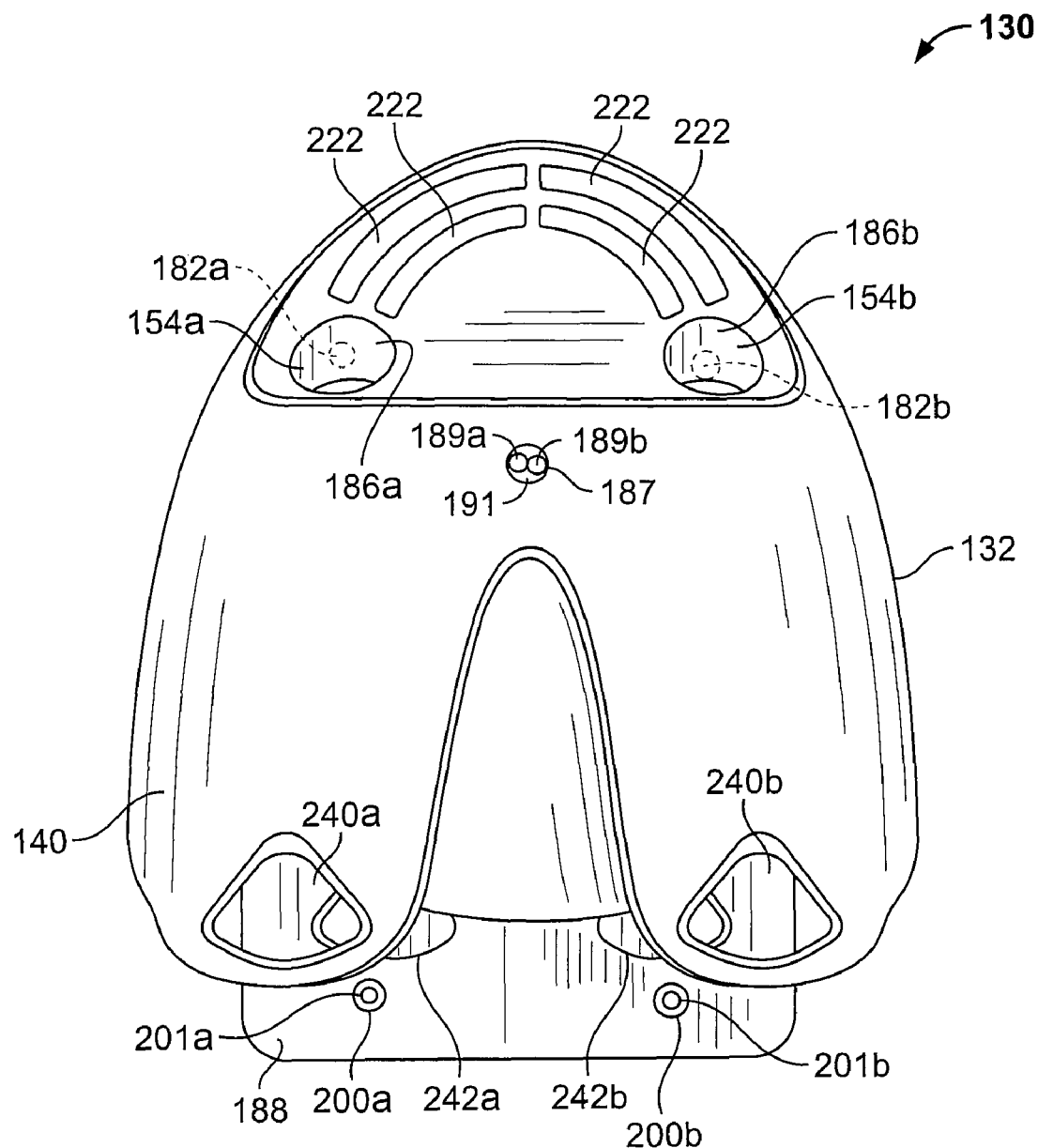
Figure 28:
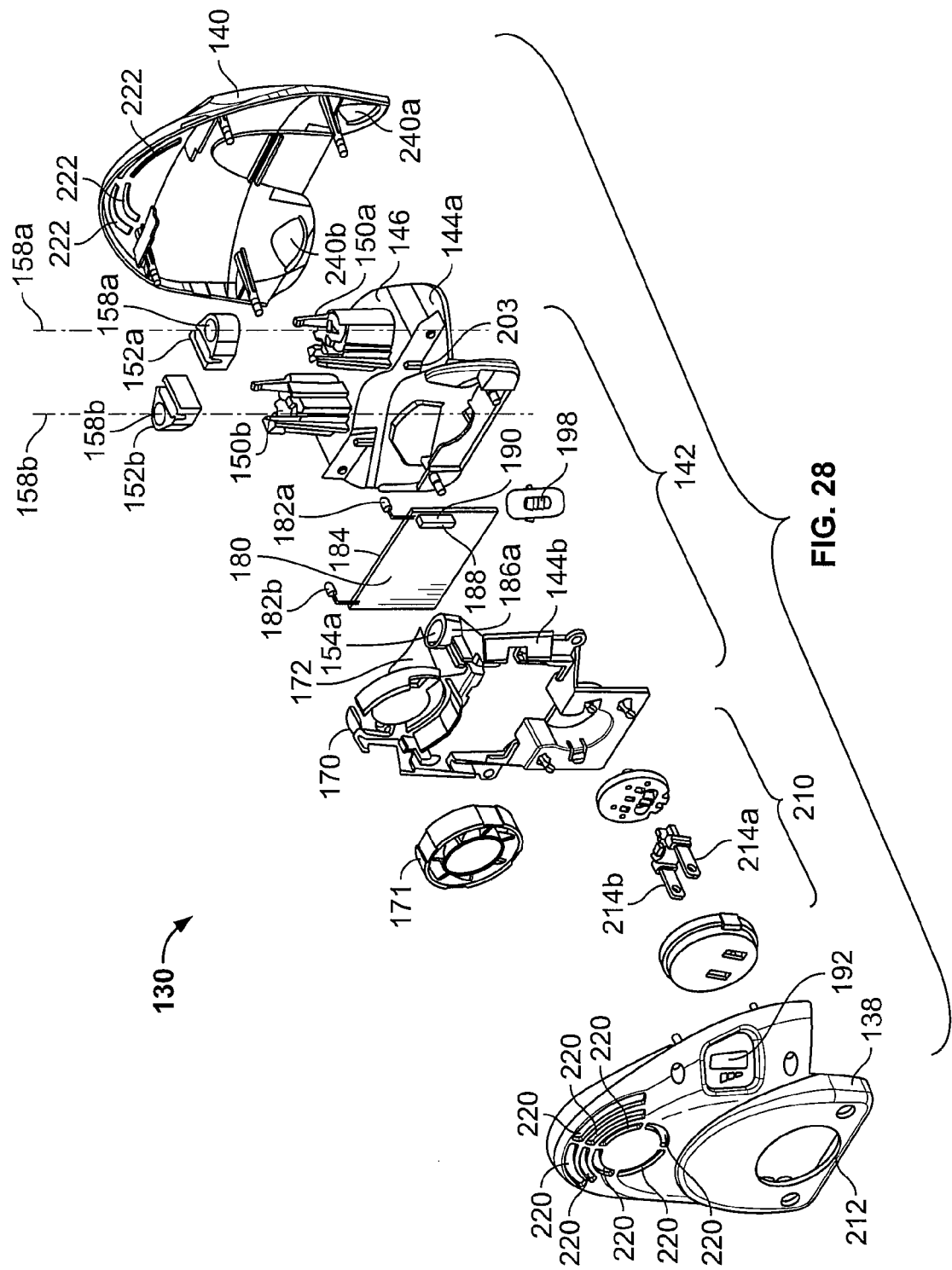
FIG. 28 is an exploded view of the diffuser of FIG. 25.

A further embodiment of a volatile material diffuser 130 is depicted in FIGS. 25-28. The diffuser 130 is similar to and works in the same manner as any of the diffusers 30 herein. As seen in FIG. 25, the diffuser 130 includes a housing 132 for holding two containers 134a, 134b having volatile materials 135a, 135b therein and wicks 136a, 136b extending therefrom. As best seen in FIG. 28, the housing 132 includes a rear portion 138, a cover portion 140, and a mounting structure 142. The mounting structure 142 is attached to the rear portion 138 and the cover portion 140 is mounted to the rear portion 138 and the mounting structure 142 such that the mounting structure 142 is disposed between the rear and cover portions 138, 140. Referring to FIG. 28, the mounting structure 142 includes front and rear portions 144a, 144b, wherein the front portion 144a includes a horizontal surface 146 having first channels 150a, 150b extending therethrough, ring heaters 152a, 152b disposed atop structures forming the first channels 150a, 150b, and second channels 154a, 154b positioned over the ring heaters 152a, 152b. The heaters 152a, 152b are disposed above the first channels 150a, 150b, and the second channels 154a, 154b are disposed above the heaters 152a, 152b. Ring channels 156a, 156b formed through the ring heaters 152a, 152b, the first channels 150a, 150b, and the second channels 154a, 154b are all aligned along vertical axes 158a, 158b. A fan supporting structure 170 having a fan 171 therein extends upwardly from the rear portion 144b of the mounting structure 142 above the second channels 154a, 154b and a semi-circular structure 172 is disposed between the second channels 154a, 154b below the fan 170. The semi-circular structure 172 prevents air flow from the fan 170 from circulating throughout the diffuser 130.

As seen in FIG. 28, a printed circuit board (PCB) 180 is secured within the rear portion 144b of the mounting structure 142 and includes all circuitry to control the diffuser 130. First and second light emitting diodes (LEDs) 182a, 182b extend from an upper edge 184 of the PCB 180 and are disposed adjacent rear surfaces 186a, 186b of the second channels 154a, 154b. When the LED's 182a, 182b are illuminated, the light can be seen through the rear surfaces 186a, 186b, respectively. The LEDs 182a, 182b may be illuminated when respective heaters 152a, 152b are actuated. Alternatively, a light source 187 may be disposed at any location within the diffuser 130. The light source 187 may include first and second colored LEDs 189a, 189b disposed with a single lens 191 in the form of a diffuser, as seen in FIGS. 25 and 27. The LEDs may be of any color, but in a specific example, a first of the LEDs 189a is red and a second of the LEDs 189b is blue. If a first of the heaters 152a is activated, the first LED 189a is illuminated to project a red color, if a second of the heaters 152b is activated, the second LED 189b is illuminated to project a blue color, if neither of the heaters 152a, 152b is activated, neither of the LEDs 189a, 189b is illuminated, and if both of the heaters 152a, 152b are activated, both of the LEDs 189a, 189b are illuminated to create a blended purple color. This feature provides a visual color indication to a user of what volatile materials are being emitted and an indication of when changes in volatile materials have occurred. Optionally, a single LED that emits multiple colors can be utilized to provide the same feature.

In addition to or in place of the LEDs 182a, 182b, and/or the light source 187, light sources 200a, 200b, as seen in FIG. 27, may be disposed behind the containers 134a, 134b, such that light from the light sources 200a, 200b shines through the containers 134a, 134b and the volatile materials 135a, 135b therein when illuminated. The light sources 200a, 200b include a single LED 201a, 201b. The LEDs 201a, 201b may project colored or white light and/or each LED 201a, 201b may project the same or different colored light. Optionally, the light sources 200a, 200b may include any number of LEDs, any of which may be colored. In one embodiment, each light source 200a, 200b includes multiple different colored LEDs that are illuminated to produce a light show. When a particular heater 152a, 152b is activated, an associated light source 200a, 200b is activated to indicate to the user which volatile material 135a, 135b is being emitted.

Referring to FIG. 28, a light source 203 may be disposed on a lower surface of the horizontal surface 146. In such case, the light source 203 would shine downwardly onto the containers 134a, 134b. In such embodiment, the light source 203 includes either multiple LEDs or a multi-colored LED. As the volatile material being automatically changed, a color emitted by the light source 203 may also change. In a non-limiting example wherein the heaters 152*a*, 152*b* are activated and deactivated at the same time and the light source 203 includes a tricolored LED, while the first heater 152*a* is activated to emit the first volatile material 135*a*, a red color may be emitted from the light source 203. When the first heater 152*a* deactivates and the second heater 152*b* activates, the red color is replaced with a blue color or morphs into the blue color. This change in color of the light source 203 indicates to the user that a new volatile material is being emitted, but not necessarily which volatile material is being emitted.

Still referring to FIG. 28, an intensity level switch 188 extends from the PCB 180 and includes an actuator arm 190 that extends through an aperture 192 in the rear portion 138 of the housing 132. A button 194 is disposed over the actuator arm 190 to change a position of the switch 188. The position of the switch 188 is sensed by the PCB 180 and an intensity level at which the volatile materials 135*a*, 135*b* are emitted is varied based on the position of the switch 188. As the intensity level is varied, an intensity of the LEDs and/or light sources 182*a*, 182*b*, 189*a*, 189*b*, 201*a*, 201*b*, and/or 203 may be varied. In particular, if the diffuser 130 is set at a highest intensity level, the LEDs and/or light sources 182*a*, 182*b*, 189*a*, 189*b*, 201*a*, 201*b*, and/or 203 associated with the activated heaters 152*a*, 152*b* are illuminated at their highest intensity level, if the diffuser 130 is set at a lowest intensity level, the LEDS and/or light sources 182*a*, 182*b*, 189*a*, 189*b*, 201*a*, 201*b*, and/or 203 associated with the activated heaters 152*a*, 152*b* are illuminated at their lowest intensity level, and for any intensity levels in between, the LEDs and/or light sources 182, 182*b*, 189*a*, 189*b*, 201*a*, 201*b*, and/or 203 associated with the activated heaters 152*a*, 152*b* are illuminated at respective intensity levels. Optionally, two intensity level switches 188 may be utilized, wherein each switch 188 controls the intensity level of a particular volatile material 135*a*, 135*b* associated with a particular heater 152*a*, 152*b*.

Alternatively, or in addition to the intensity level switch 188, a volatile material selector switch (not shown) or another type of switch may be utilized. The volatile material selector switch would allow a user to select to emit a first of the volatile materials 135*a*, a second of the volatile materials 135*b*, or both of the volatile materials 135*a*, 135*b* in an alternating sequence.

The diffuser 130 or any of the diffusers herein may include an odor sensor that senses an amount of volatile material in the diffuser 130. If the sensor no longer detects volatile materials, meaning that containers 136*a*, 136*b* are empty or have little volatile material 135*a*, 135*b* therein, the sensor can notify the PCB 180. In response to a notification, the PCB 180 indicates to the user that one or more of the containers 136*a*, 136*b* need to be replaced, such as by deactivating the LEDs 182*a*, 182*b* and/or 189*a*, 189*b*, deactivating the heaters 152*a*, 152*b*, and/or illuminating one or more LEDs 182*a*, 182*b* and/or 189*a*, 189*b* in a different color, such as yellow or black. In another embodiment, the diffuser 130 or any of the diffusers herein may include a membrane 202*a*, 202*b* as seen in FIG. 25 within the container 134*a*, 134*b*, preferably along at least a portion of an inner surface of the container 134*a*, 134*b*. When volatile materials 135*a*, 135*b* are disposed within the containers 134*a*, 134*b*, the membranes 202*a*, 202*b* are wet and transparent. As the volatile materials 135*a*, 135*b* are dispensed from the containers 134*a*, 134*b*, the membranes 202*a*, 202*b* begin to dry out and become opaque. The opaque nature of the membrane 202*a*, 202*b* indicates to the user that the container 134*a*, 134*b* needs to be replaced. If LEDs 201*a*, 201*b* (FIG. 27) are disposed behind the containers 134*a*, 134*b*, light from the LEDs 201*a*, 201*b* appears more like a point source when the containers 134*a*, 134 are full (and the membranes 202*a*, 202*b* are transparent) and light from the LEDs 201*a*, 201*b* appears as a blended source when the containers 134*a*, 134*b* are empty or nearly empty (and the membranes 202*a*, 202*b* are opaque).

As seen in FIG. 28, a plug assembly 210 is connected to the rear portion 144*b* of the mounting structure 142 and extends through an aperture 212 in the rear portion 138 of the housing 132. Electrical blades 214*a*, 214*b* of the plug assembly 210 are inserted into an electrical socket to power the diffuser 130.

Referring to FIGS. 25-27, the rear portion 138 of the housing 132 includes a plurality of inflow vents 220 and the cover portion 140 includes a plurality of outflow vents 222. Although the vents 220, 222 are shown in a particular semicircular configuration, any suitable configuration is possible. The fan 170 is disposed between the inflow and outflow vents 220, 222 such that, when the fan 170 is running, air is pulled in through the inflow vents 220 and air is pushed out the outflow vents 222 to circulate the volatile materials 135*a*, 135*b*, as they are emitted.

Referring to FIG. 28, the containers 134*a*, 134*b*, as seen in FIG. 25 are inserted into the diffuser 130 by inserting portions of the wicks 136*a*, 136*b* that extend out of the respective containers 134*a*, 134*b* through the first channels 150*a*, 150*b* and the ring channels 156*a*, 156*b*, respectively, such that the wicks 136*a*, 136*b* reside in same and gaps are formed between the wicks 136*a*, 136*b* and walls forming the first channels 150*a*, 150*b* and the ring channels 156*a*, 156*b*. When the fan 170 is activated, airflow therefrom flows over the second channels 154*a*, 154*b*, causing a chimney effect and allowing air to flow downwardly through the second channels 154*a*, 154*b* and through the gaps formed between the wicks 136*a*, 136*b* and the first channels 150*a*, 150*b* and the ring channels 156*a*, 156*b*, thereby cooling the wicks 136*a*, 136*b* and/or heaters 152*a*, 152*b*. Referring to FIGS. 25, 27, and 28, the containers 134*a*, 134*b* are retained within the diffuser 130 by opposing shell-shaped apertures 240*a*, 240*b* and shell-shaped grooves 242*a*, 242*b*. In particular, as the containers 134*a*, 134*b* are inserted into the diffuser 130, shell-shaped protrusions 244*a*, 244*b* on opposing sides of the containers 134*a*, 134*b*, respectively, slide into opposing apertures 240*a*, 240*b* and grooves 242*a*, 242*b*, wherein the containers 134*a*, 134*b* must be pulled downwardly to overcome an interference formed by walls forming the apertures 240*a*, 240*b* and grooves 242*a*, 242*b*.

Figure 29:
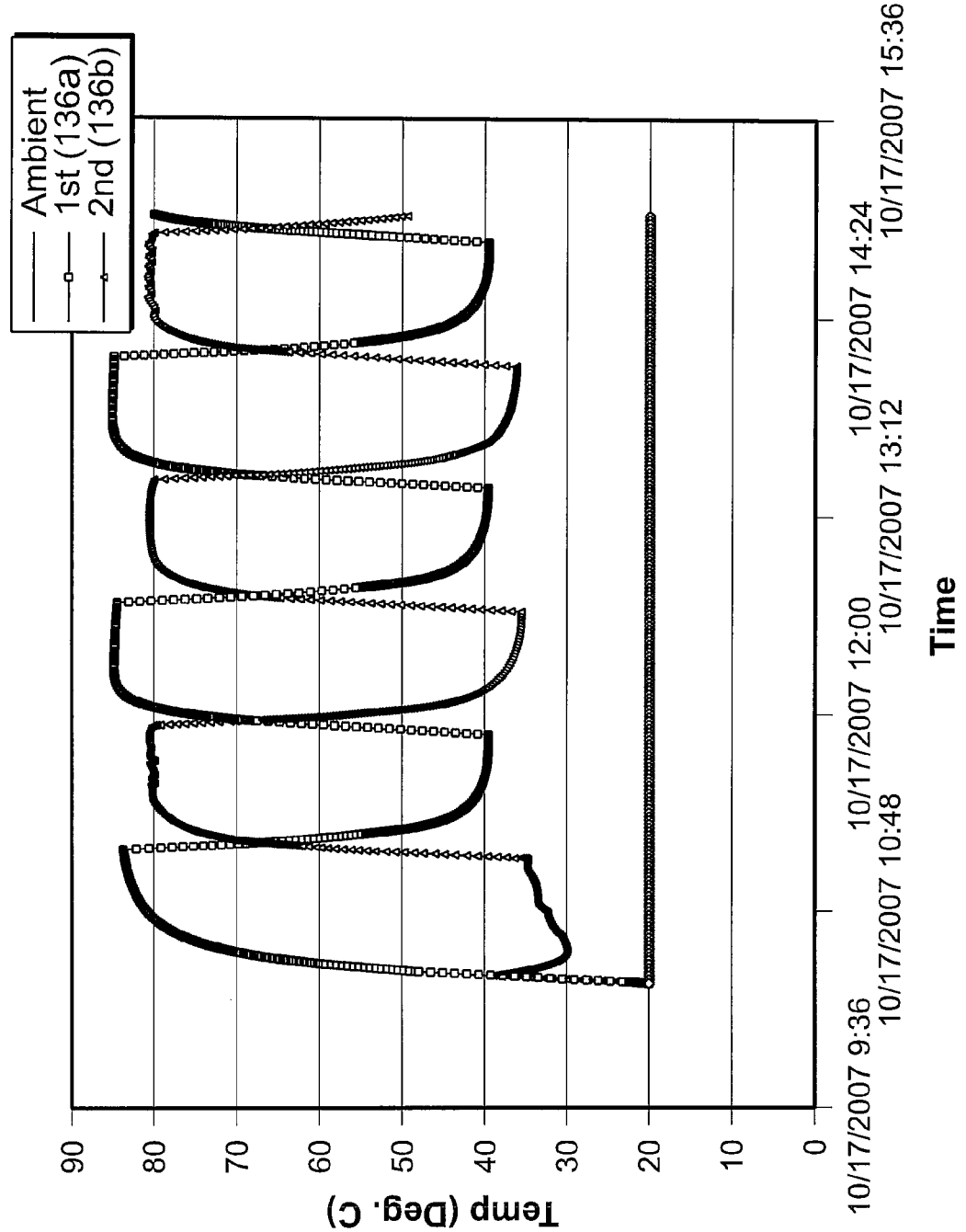
FIG. 29 is a graphical representation depicting temperature versus time for the diffuser of FIGS. 25-28 with a fan thereof turned off.
Figure 30:
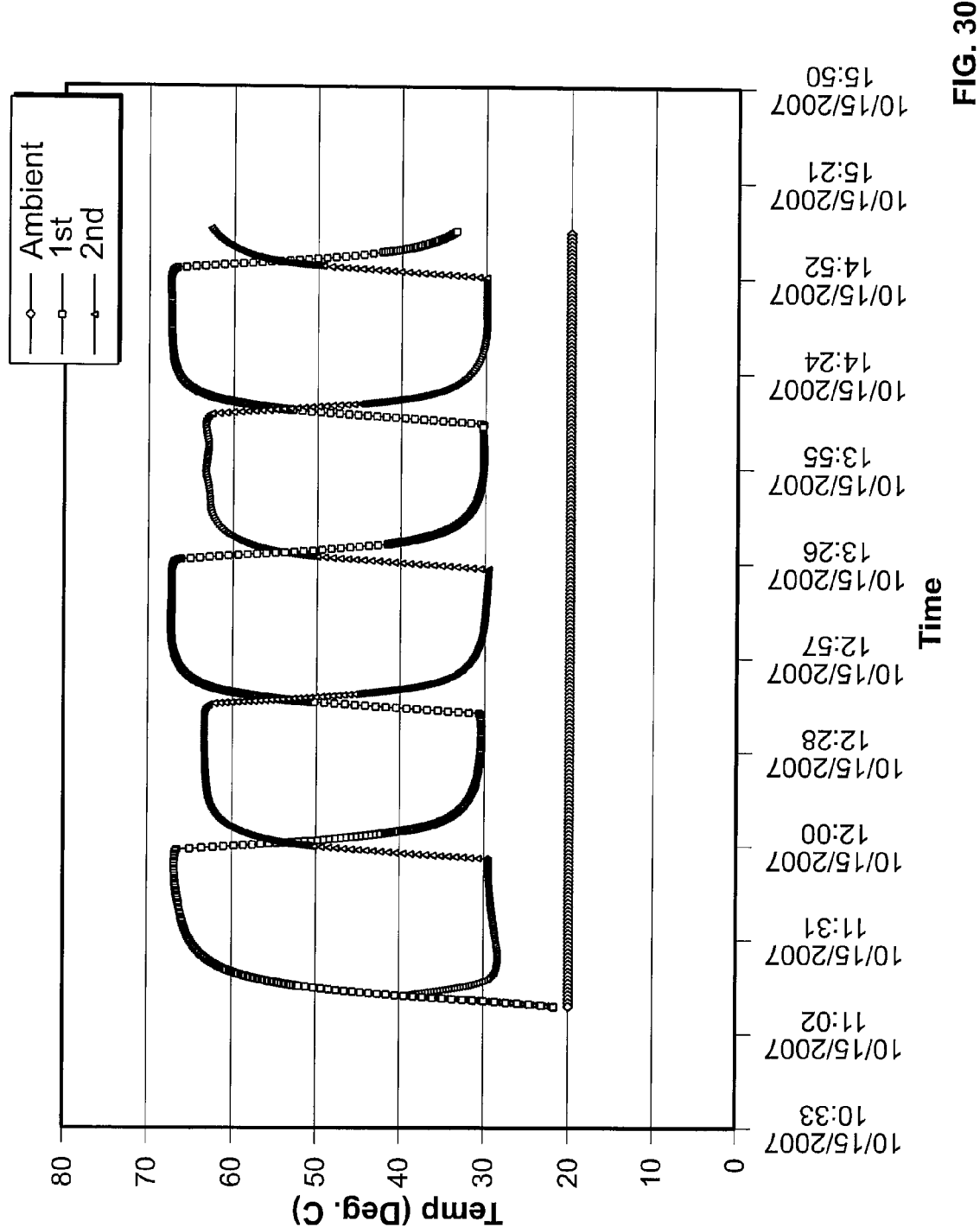

The diffuser 130 of FIGS. 25-28 was tested with the fan 170 on and with the fan 170 off. The test results of FIGS. 29 and 30 were generated by using the same methodology as described above. The graph of FIG. 29 depicts temperature versus time for the diffuser 130 with the fan 170 turned off. As seen from the results, the maximum temperatures for each of the wicks 136*a*, 136*b* are between about 80 degrees Celsius and about 85 degrees Celsius (between about 176 and about 185 degrees Fahrenheit) and the minimum temperatures for each of the wicks during the testing period are between about 36 degrees Celsius and about 39 degrees Celsius (between about 97 and about 102 degrees Fahrenheit). Referring next to FIG. 30, in which the fan 170 was turned on, the maximum temperatures for the wicks 136*a*, 136*b* is between about 63 and about 67 degrees Celsius (between about 145 and about 153 degrees Fahrenheit) and the minimum temperatures for the wicks 136*a*, 136*b* during the same period is between about 29 and about 31 degrees Celsius (between about 84 and about 88 degrees Fahrenheit). During the test periods of FIGS. 29 and 30, ambient temperature was about 20 degrees Celsius (about 68 degrees Fahrenheit). As with the test results above, the fan 170 provides cooling for the wicks 136a, 136b and/or heaters 152a, 152b, such that the amount of volatile material associated with a deactivated heater 152a, 152b that is emitted is minimized, preferably to a point that such volatile material is not sensed by a user.

Although a fan 50, 100a, 100b, or 170 is utilized in the embodiments as discussed above, any means for providing a flow of air could be utilized including, but not limited to, an axial propeller-type fan, a centrifugal-type squirrel cage blower, a peristaltic pump, or any other fans or pumps known in the art.

INDUSTRIAL APPLICABILITY

The present application provides a volatile material diffuser for emitting more than one volatile material therefrom, wherein the volatile materials are emitted in an alternating sequence. The volatile materials are vaporized by heaters and a fan aids in exhausting the vaporized materials from the diffuser. An air flow from the fan also cools the heaters and associated wicks containing the volatile materials after they have been deactivated such that the amount of the overlap of volatile materials is minimized. One or more LEDs may be incorporated into a diffuser to indicate which volatile material (s) is being emitted, to provide a visual effect, to indicate that the volatile material being emitted has changed, and/or to aid in indicating to a user that a container containing a volatile material needs to be replaced.

Numerous modifications will be apparent to those skilled in the art in view of the foregoing description. Accordingly, this description is to be construed as illustrative only and is presented for the purpose of enabling those skilled in the art to make and use the present application and to teach the best mode of carrying out same. All patents and other references cited herein are incorporated by reference in their entirety. The exclusive rights to all modifications which come within the scope of the appended claims are reserved.

We claim:

1. A volatile material diffuser, comprising:
    a housing;
    first and second containers holding first and second volatile materials and having first and second wicks, respectively, in contact with respective volatile materials and extending out of respective containers, wherein the containers are inserted into and detachably attached to the housing;
    first and second heaters disposed within the housing adjacent the first and second wicks, respectively, to vaporize the first and second volatile materials, respectively; and
    means for providing an air flow disposed in the housing such that air from the means to provide air flow transports vaporized volatile materials away from the housing;
    wherein the heaters are energized in an alternating sequence such that when a heater is deactivated, the means for providing an air flow cools a wick associated with the deactivated heater;
    wherein the means for providing an air flow is a fan that is alternated between first and second different speeds and wherein the first speed is greater than the second speed such that the first speed provides a burst of the volatile material for a larger detection area and the second speed provides a more concentrated emission in a smaller detection area.

2. The device of claim 1, wherein the means for providing an air flow is a fan that cools the wicks associated with deactivated heaters to a temperature that is closer to ambient temperature than the wicks would be cooled without the fan.

3. The device of claim 2, wherein the fan is angled upwardly at an angle of between about 0 degrees and about 45 degrees with respect to a longitudinal axis of the diffuser.

4. The device of claim 1, wherein the means for providing an air flow is a fan that is energized continuously and runs at one speed.

5. The device of claim 1 further including a second means for providing an air flow, wherein the first-named means is associated with the first heater and the second means is associated with the second heater, the first-named means is energized for a period of time when the first heater is deactivated, and the second means is energized for the period of time when the second heater is deactivated, and wherein the period of time is less than a period of time that the first and second heaters are activated.

6. The device of claim 1 further including a light source having first and second light emitting diodes (LEDs) of first and second different colors, respectively, and disposed within a single lens that forms a diffuser, wherein when the first heater is activated, a first of the LEDs is illuminated, when the second heater is activated, a second of the LEDs is illuminated, when the first and second heaters are activated, the first and second LEDs are illuminated to form a third different color, and when neither of the first and second heaters is activated, neither of the LEDs is illuminated.

7. The device of claim 1 further including a first light emitting diode (LED) disposed within the housing behind the first container and a second LED disposed within the housing behind the second container, wherein when the first heater is activated, the first LED is illuminated and when the second heater is activated, the second LED is illuminated.

8. The device of claim 7, wherein each of the containers includes a membrane on an inner surface thereof that is wet and transparent when volatile materials are disposed within the containers and wherein, as the volatile materials are dispensed, the membranes dry out and become opaque to indicate to a user that one or more of the containers needs to be replaced.

9. The device of claim 8, wherein the first and second LEDs appear as a point source when the membranes are transparent and appear as a blended source of light to the user when the membranes are opaque, thereby indicating that one or more of the containers needs to be replaced.

10. The device of claim 1, further including an odor sensor that senses an amount of volatile material within one or more of the containers within the diffuser, wherein when the sensor detects that there is little or no volatile material left in one or more of the containers, the sensor can notify a printed circuit board disposed within the device to activate or deactivate a light emitting diode or turn off one or more of the heaters.

11. A volatile material diffuser, comprising:
    a housing;
    first and second containers holding first and second volatile materials and having first and second wicks, respectively, in contact with respective volatile materials and extending out of respective containers, wherein the containers are inserted into and detachably attached to the housing;
    first and second heaters disposed within the housing adjacent the first and second wicks, respectively, to vaporize the first and second volatile materials, respectively; and
    a fan disposed in the housing such that air from the fan exhausts vaporized volatile materials from the housing;
    wherein when the first heater is deactivated and the second heater is activated, the fan acts to cool the first wick to reduce temperatures of the first wick and the first heater to minimize the amount of the first volatile material that is emitted while the second volatile material is being emitted;

wherein the fan is energized for a period of time after the deactivation of each heater to aid in cooling the deactivated heater and the wick associated with the deactivated heater and wherein the period of time is between about 30 seconds and about 5 minutes.

12. The device of claim 11, wherein when the second heater is deactivated and the first heater is activated, the fan acts to cool the second wick to reduce temperatures of the second wick and the second heater to minimize the amount of the second volatile that is emitted while the first volatile material is being emitted.

13. The device of claim 11, wherein the fan is energized continuously, alternating between first and second speeds, the first speed being greater than the second speed, and wherein when one heater is deactivated and the other is activated, the fan is energized to the first speed.

14. The device of claim 11, wherein the fan is at zero degrees with respect to a vertical axis of the diffuser.

15. The device of claim 11, wherein the fan is angled upwardly at an angle of 22.5 degrees with respect to a vertical axis of the diffuser.

16. A volatile material diffuser, comprising:
a housing;
first and second containers holding first and second volatile materials and having first and second wicks, respectively, in contact with respective volatile materials and extending out of respective containers, wherein the containers are inserted into and detachably attached to the housing;
first and second heaters disposed within the housing adjacent the first and second wicks, respectively, to vaporize the first and second volatile materials, respectively; and
means for providing an air flow disposed in the housing such that air from the means to provide air flow transports vaporized volatile materials away from the housing;
wherein the heaters are energized in an alternating sequence such that when a heater is deactivated, the means for providing an air flow cools a wick associated with the deactivated heater;
wherein the means for providing an air flow is disposed in a first chamber, the wicks and heaters are disposed in a second chamber separate from the first chamber, the wicks are disposed in channels formed within the second chamber, and the air flow moves air through gaps formed by channel walls and the wicks to thereby cool the wicks and heaters.

17. The device of claim 16, wherein the fan is angled upwardly at an angle of between about 0 degrees and about 45 degrees with respect to a longitudinal axis of the diffuser.

18. The device of claim 17, wherein the fan is angled upwardly at an angle of 22.5 degrees with respect to a vertical axis of the diffuser.

19. The device of claim 16, wherein when the second heater is deactivated and the first heater is activated, the fan acts to cool the second wick to reduce temperatures of the second wick and the second heater to minimize the amount of the second volatile that is emitted while the first volatile material is being emitted.

20. The device of claim 16, wherein the fan is energized continuously, alternating between first and second speeds, the first speed being greater than the second speed, and wherein when one heater is deactivated and the other is activated, the fan is energized to the first speed.

* * * * *